US012782311B2

(12) United States Patent
Bedau

(10) Patent No.: US 12,782,311 B2
(45) Date of Patent: Nov. 3, 2026

(54) LOW NOISE AMPLIFIERS WITH FEEDBACK FOR NANOPORE APPLICATIONS

(71) Applicant: Western Digital Technologies, Inc., San Jose, CA (US)

(72) Inventor: Daniel Bedau, San Jose, CA (US)

(73) Assignee: Western Digital Technologies, Inc., San Jose, CA (US)

(*) Notice: Subject to any disclaimer, the term of this patent is extended or adjusted under 35 U.S.C. 154(b) by 270 days.

(21) Appl. No.: 18/590,557

(22) Filed: Feb. 28, 2024

(65) Prior Publication Data

US 2024/0201120 A1 Jun. 20, 2024

Related U.S. Application Data

(63) Continuation of application No. 17/651,254, filed on Feb. 16, 2022, now Pat. No. 11,946,894.

(51) Int. Cl.
*G01N 27/22* (2006.01)
*C12Q 1/6869* (2018.01)
(Continued)

(52) U.S. Cl.
CPC ......... *G01N 27/228* (2013.01); *C12Q 1/6869* (2013.01); *G01N 27/226* (2013.01);
(Continued)

(58) Field of Classification Search
CPC ............... G01N 27/228; G01N 27/226; G01N 33/48721; C12Q 1/6869; H03F 3/04; H03F 2200/294
See application file for complete search history.

(56) References Cited

U.S. PATENT DOCUMENTS

| | | | |
|---|---|---|---|
| 7,075,161 | B2 | 7/2006 | Barth |
| 8,669,124 | B2 | 3/2014 | Merz |

(Continued)

FOREIGN PATENT DOCUMENTS

| | | | |
|---|---|---|---|
| CA | 2869753 | A1 | 10/2013 |
| CN | 209342031 | | 9/2019 |

(Continued)

OTHER PUBLICATIONS

B. Goldstein, D. Kim, M. Magoch, Y. Astier and E. Culurciello, "CMOS low current measurement system for nanopore sensing applications," 2011 IEEE Biomedical Circuits and Systems Conference (BioCAS), 2011, pp. 265-268, doi: 10.1109/BioCAS.2011.6107778.
Beamish, E., Kwok, H., Tabard-Cossa, V., Godin, M. "Fine-tuning the Size and Minimizing the Noise of Solid-state Nanopores." J. Vis. Exp. (80), e51081, doi:10.3791/51081 (2013).

(Continued)

*Primary Examiner* — Alvaro E Fortich

(57) ABSTRACT

Disclosed herein are devices, systems, and methods that can improve the SNR of nanopore measurements by mitigating the effect of parasitic capacitance between the sense electrode and the counter electrode. In some embodiments, a feedback circuit is used to inject a charge into the sense electrode to at least partially cancel the parasitic capacitance between the sense electrode and the counter electrode. In some embodiments, bootstrapping of a signal from the amplifier output or from the sense electrode is used to inject a charge on the counter electrode to substantially cancel the parasitic capacitance.

23 Claims, 16 Drawing Sheets

(51) Int. Cl.
*G01N 33/487* (2006.01)
*H03F 3/04* (2006.01)

(52) U.S. Cl.
CPC ......... *G01N 33/48721* (2013.01); *H03F 3/04* (2013.01); *H03F 2200/294* (2013.01)

(56) References Cited

U.S. PATENT DOCUMENTS

| | | | |
|---|---|---|---|
| 8,860,438 B2 | 10/2014 | Zhang | |
| 9,217,727 B2 | 12/2015 | Rosenstein et al. | |
| 9,322,820 B2 | 4/2016 | Blick et al. | |
| 9,650,670 B2 | 5/2017 | Kim et al. | |
| 9,869,702 B2 | 1/2018 | Kuramochi et al. | |
| 11,181,504 B2 | 11/2021 | Washizu et al. | |
| 11,571,148 B1 | 2/2023 | Puttananjegowda et al. | |
| 11,624,727 B2 | 4/2023 | Rosenstein et al. | |
| 11,833,346 B2 | 12/2023 | Park et al. | |
| 2008/0248561 A1 | 10/2008 | Golovchenko et al. | |
| 2011/0133255 A1 | 6/2011 | Merz | |
| 2013/0048499 A1 | 2/2013 | Mayer et al. | |
| 2013/0180867 A1 | 7/2013 | Rosenstein et al. | |
| 2014/0048416 A1 | 2/2014 | Rosenstein et al. | |
| 2014/0221249 A1* | 8/2014 | Chen | G01N 33/48721 506/12 |
| 2015/0060276 A1 | 3/2015 | Golovchenko et al. | |
| 2015/0060277 A1 | 3/2015 | Golovchenko et al. | |
| 2015/0337367 A1 | 11/2015 | Kim et al. | |
| 2015/0369776 A1 | 12/2015 | Rosenstein et al. | |
| 2015/0377856 A1 | 12/2015 | Dunbar et al. | |
| 2016/0154032 A1 | 6/2016 | Kuramochi | |
| 2017/0145481 A1* | 5/2017 | Kim | H03F 3/45076 |
| 2018/0238824 A1 | 8/2018 | Lee et al. | |
| 2019/0004027 A1* | 1/2019 | Chen | G01N 33/48721 |
| 2019/0154623 A1 | 5/2019 | Chen | |
| 2020/0033292 A1* | 1/2020 | Washizu | G01N 15/132 |
| 2020/0292594 A1 | 9/2020 | Hsu et al. | |
| 2021/0148886 A1 | 5/2021 | Maney, Jr. | |
| 2021/0300750 A1 | 9/2021 | Waterman | |
| 2023/0172495 A1 | 6/2023 | Puttananjegowda et al. | |

FOREIGN PATENT DOCUMENTS

| | | |
|---|---|---|
| CN | 111090002 A | 5/2020 |
| CN | 112292462 A | 1/2021 |
| CN | 112924745 A | 6/2021 |
| EP | 2734839 A1 | 5/2014 |
| EP | 2815425 A4 | 10/2015 |
| KR | 102059488 B1 | 12/2019 |
| WO | 2010020912 A1 | 2/2010 |
| WO | 2012116161 A1 | 8/2012 |
| WO | 2014066909 A1 | 5/2014 |
| WO | 2020183172 A1 | 9/2020 |

OTHER PUBLICATIONS

C. Hoyle and A. Peyton, "Bootstrapping techniques to improve the bandwidth of transimpedance amplifiers," IEE Colloquium on Analog Signal Processing (Ref. No. 1998/472), 1998, pp. 7/1-7/6, doi: 10.1049/ic:19980849.

Camilla L.C. Ip et al., "MinION Analysis and Reference Consortium: Phase 1 data release and analysis," F1000Research 2015, 4:1075 Last updated: May 23, 2017.

Ciccarella, P., Carminati, M., Ferrari, G., Fraccari, R.L., & Bahrami, A. "Integrated low-noise current amplifier for glass-based nanopore sensing." 2014 10th Conference on Ph.D. Research in Microelectronics and Electronics (PRIME), 1-4 (2014).

D. V. Barkovaa et al., "Channel and Motor Proteins for Translocation of Nucleic Acids in Nanopore Sequencing," ISSN 0027-1314, Moscow University Chemistry Bulletin, 2020, vol. 75, No. 3, pp. 149-161.

International Search Report and Written Opinion from PCT Application No. PCT/US2022/030440 (filed May 22, 2022), mailed Nov. 3, 2022.

International Search Report and Written Opinion from PCT Application No. PCT/US2022/030441 (filed May 22, 2022), mailed Dec. 1, 2022.

J. Rosenstein, V. Ray, M. Drndic and K. L. Shepard, "Solid-state nanopores integrated with low-noise preamplifiers for high-bandwidth DNA analysis," 2011 IEEE/NIH Life Science Systems and Applications Workshop (LiSSA), 2011, pp. 59-62, doi: 10.1109/LISSA.2011.5754155.

P. Horowitz and W. Hill, "The Art of Electronics, 3rd Edition," Cambridge University Press, 2015.

Patrick S Spinney et al., "Fabrication and characterization of a solid-state nanopore with self-aligned carbon nanoelectrodes for molecular detection," Nanotechnology, vol. 23, No. 13, 2012.

Rosenstein, J., Wanunu, M., Merchant, C. et al. "Integrated nanopore sensing platform with sub-microsecond temporal resolution." Nat Methods 9, 487-492 (2012). https://doi.org/10.1038/nmeth.1932.

Shengfa Liang et al., "Noise in nanopore sensors: Sources, models, reduction, and benchmarking," Nanotechnology and Precision Engineering 3 (2020) 9-17.

Stephen Jordan Fleming, "Probing nanopore—DNA interactions with MspA," Nov. 2017.

V. Dimitrov et al., "Nanopores in solid-state membranes engineered for single molecule detection," Nanotechnology, vol. 21, No. 6, Jan. 11, 2010.

Yun et al. "An integrated potentiostat sensor with digitally-controlled input-parasitic compensation fornanopore applications." In: 2015 IEEE Sensors, IEEE, Nov. 4, 2015, pp. 1-4.

Zhen Gu, "Ultra-low noise measurements of nanopore-based single molecular detection," Sep. 2017, Science Bulletin 62(18).

Rosenstein, J.K., et al., "Temporal resolution of nanopore sensor recordings", 35th Annual International Conference of the IEEE, pp. 4110-4113, (Jul. 3-7, 2013).

Chi, Y.M., et al., "Ultra-High Input Impedance, Low Noise Integrated Amplifier for Noncontact Biopotential Sensing" IEEE Journal, vol. 1, Issue No. 4, pp. 526-535, (Dec. 2011).

* cited by examiner

LOW NOISE AMPLIFIERS WITH FEEDBACK FOR NANOPORE APPLICATIONS

CROSS-REFERENCE TO RELATED APPLICATIONS

This application is a continuation of U.S. application Ser. No. 17/651,254, filed Feb. 16, 2022 and entitled "LOW NOISE AMPLIFIERS WITH FEEDBACK FOR NANOPORE APPLICATIONS", which incorporates by reference for all purposes in its entirety U.S. patent application Ser. No. 17/651,257, filed Feb. 16, 2022 and entitled "LOW NOISE AMPLIFIERS WITH SHIELDS FOR NANOPORE APPLICATIONS", which published on Aug. 17, 2023 as U.S. Patent Pub. No. 2023/0258592.

U.S. application Ser. No. 17/651,254 and U.S. Patent Pub. No. 2023/0258592 are hereby incorporated by reference in their entireties for all purposes.

BACKGROUND

Nanopores are small holes, typically 1-2 nanometers (nm) in diameter and a couple of nanometers thick, that can be used to observe single molecules at high throughput and with relatively fine temporal resolution. Nanopores can be used to read molecules (e.g., biomolecules) for applications such as DNA sequencing, DNA/RNA storage applications, and bioanalytical sensing.

There are two types of nanopore: biological nanopores (also referred to as protein nanopores) and solid-state nanopores. A biological nanopore is made from a pore material embedded in a lipid membrane. A solid-state nanopore is a nanoscale (e.g., nanometer-sized) opening in a synthetic membrane (e.g., SiNx, $SiO_2$, etc.).

A target molecule in an electrolyte solution can be driven through a nanopore (either biological or solid-state) by electrophoresis. A highly-focused external electric field applied transverse to and in the vicinity of the nanopore (e.g., by electrodes used to read or detect the molecule) acts on a relatively short segment of the negatively charged molecule and directs it through the hole in the nanopore.

An ionic current can be generated across the nanopore by applying a bias voltage. As a molecule passes through a nanopore, the ions occupying the pore are displaced, which causes changes in the ionic current measured across the nanopore. These changes in the ionic current can be observed and used to detect constituent parts of the molecule (e.g., nucleotides of a DNA strand). For example, by analyzing the amplitudes, durations, frequencies, and/or shapes of the blockade events, various properties of the target molecule can be deduced.

As a specific example, as nucleic acid moves, or translocates, through a nanopore, different nucleotides cause different ionic current patterns. Specifically, the nucleotides cause distinct, measurable ionic current blockades, or current drops, as they pass through the nanopore. The current blockades can be recorded (e.g., using a current amplifier) and converted into digital signals (e.g., using an analog-to-digital converter). These current blockades, or patterns of them, can be used to distinguish between different nucleotides.

One challenge with using nanopores is that detection relies on the ability to detect small differences in the ionic current (e.g., on the order of picoamperes) as a molecule translocates through the nanopore. Noise in the ionic current measurement limits the signal-to-noise ratio (SNR) and the effective time resolution of the detection. The noise is dependent on any capacitance present at the input to the amplifier that senses and amplifies the ionic current signal. For solid-state nanopores, the total capacitance includes the capacitance of the thin membrane in which the nanopore is fabricated, the capacitance of the wiring between the electrodes and the amplifier, and the characteristic capacitance of the amplifier at its input. The capacitance at the input to the amplifier forms a pole with the output impedance of the amplifier. High capacitance at the input to the amplifier can cause noise peaking and SNR degradations.

Thus, there is a need to reduce noise in the detected ionic current.

SUMMARY

This summary represents non-limiting embodiments of the disclosure.

In some aspects, the techniques described herein relate to a system for detecting molecules, the system including: a nanopore unit including a nanopore, a sense electrode, and a counter electrode; an amplifier; a feedback circuit; and control logic, wherein: the sense electrode is configured to: in cooperation with the counter electrode, detect a current associated with the nanopore, and provide the detected current to an input of the amplifier, the amplifier is configured to provide, at an output of the amplifier, a signal representing the detected current, the feedback circuit is coupled to the output of the amplifier and to the input of the amplifier, and the control logic is coupled to the feedback circuit and is configured to set at least one parameter of the feedback circuit to reduce a parasitic capacitance between the sense electrode and the counter electrode.

In some aspects, the techniques described herein relate to a system, further including: a digitizer coupled to the output of the amplifier, wherein the digitizer is configured to generate a digitized signal from the signal representing the detected current.

In some aspects, the techniques described herein relate to a system, wherein the digitizer is coupled to the control logic and is configured to provide the digitized signal to the control logic, and wherein the control logic is configured to set one or more of the at least one parameter of the feedback circuit at least in part on the digitized signal.

In some aspects, the techniques described herein relate to a system, further including memory coupled to the control logic, and wherein the control logic is further configured to retrieve a value of a first parameter of the at least one parameter from the memory and to set the first parameter to the retrieved value.

In some aspects, the techniques described herein relate to a system, further including memory, and wherein the control logic is coupled to the memory and is configured to: retrieve information from the memory, and set at least a first parameter of the at least one parameter based at least in part on the retrieved information.

In some aspects, the techniques described herein relate to a system, further including tuning logic coupled to the feedback circuit.

In some aspects, the techniques described herein relate to a system, wherein the tuning logic is configured to: adjust at least a first parameter of the at least one parameter based on an indication of a quality of the signal representing the current.

In some aspects, the techniques described herein relate to a system, wherein the indication of the quality of the signal representing the current is provided by the control logic or by a downstream process or component.

In some aspects, the techniques described herein relate to a system, further including tuning logic coupled to the output of the amplifier, and wherein the tuning logic is configured to adjust at least a first parameter of the at least one parameter based at least in part on the signal representing the current.

In some aspects, the techniques described herein relate to a system, further including tuning logic coupled to the output of the amplifier, and wherein the tuning logic is configured to: (a) adjust at least a first parameter of the at least one parameter to increase an amount of feedback provided by the feedback circuit, (b) monitor the signal representing the current, (c) in response to an indication that a signal quality associated with the signal representing the detected current is improving, adjust the first parameter to increase the amount of feedback provided by the feedback circuit, and (d) in response to detecting instability in the signal representing the current, adjust the first parameter to decrease the amount of feedback provided by the feedback circuit.

In some aspects, the techniques described herein relate to a system, further including memory, and wherein the tuning logic is further coupled to the memory and is configured to: (e) store a value of the first parameter after completing (c) and/or after completing (d).

In some aspects, the techniques described herein relate to a system, wherein a first parameter of the at least one parameter of the feedback circuit is a capacitance of the feedback circuit.

In some aspects, the techniques described herein relate to a system, wherein the feedback circuit includes a capacitor integrated with the nanopore unit, wherein the capacitor includes the sense electrode, a feedback electrode coupled to the output of the amplifier, and a feedback capacitor dielectric layer situated between the sense electrode and the feedback electrode.

In some aspects, the techniques described herein relate to a system, wherein the nanopore includes a hole, and wherein the feedback electrode is recessed from the hole.

In some aspects, the techniques described herein relate to a system, wherein the sense electrode is situated between the feedback electrode and the counter electrode.

In some aspects, the techniques described herein relate to a system, wherein the feedback electrode is situated between the sense electrode and the counter electrode.

In some aspects, the techniques described herein relate to a system, wherein the feedback circuit includes a buffer amplifier, a charge amplifier, or an AC-coupled amplifier.

In some aspects, the techniques described herein relate to a system for detecting molecules, the system including: an array including a plurality of nanopore units, each of the plurality of nanopore units including a nanopore, a sense electrode, and a counter electrode; drive circuitry coupled to the array of nanopore units; an amplifier; a multiplexer coupled to the array of nanopore units and to an input of the amplifier; a feedback circuit coupled to an output of the amplifier and to the input of the amplifier; and control logic coupled to the feedback circuit and to the multiplexer and configured to: control the multiplexer to select a first nanopore unit of the plurality of nanopore units for reading, and configure the feedback circuit to provide a first amount of feedback for the first nanopore unit.

In some aspects, the techniques described herein relate to a system, wherein the first amount of feedback is dependent on an identity of the first nanopore unit.

In some aspects, the techniques described herein relate to a system, wherein the first amount of feedback is applicable to the first nanopore unit and at least one other nanopore unit in the array.

In some aspects, the techniques described herein relate to a system, further including memory coupled to the control logic, and wherein the control logic is further configured to: retrieve information from the memory, the information associated with a prior configuration of the feedback circuit.

In some aspects, the techniques described herein relate to a system, wherein the prior configuration of the feedback circuit was a custom configuration for the first nanopore unit.

In some aspects, the techniques described herein relate to a system, further including tuning logic coupled to the feedback circuit, wherein the tuning logic is configured to: adjust at least one parameter of the feedback circuit to increase or decrease the first amount of feedback.

In some aspects, the techniques described herein relate to a system, further including tuning logic coupled to the feedback circuit, wherein the tuning logic is configured to: increase the first amount of feedback, detect an onset of instability in an amplifier output signal, and decrease the first amount of feedback in response to the detected onset of instability, thereby settling the first amount of feedback at a tuned amount of feedback.

In some aspects, the techniques described herein relate to a system, further including memory coupled to the tuning logic, and wherein the tuning logic is further configured to: store configuration information in the memory, the configuration information associated with the tuned amount of feedback.

In some aspects, the techniques described herein relate to a system, wherein the control logic is coupled to the memory, and wherein the control logic is further configured to retrieve the configuration information from the memory and to configure the feedback circuit to provide the tuned amount of feedback for the first nanopore unit.

In some aspects, the techniques described herein relate to a system, wherein the control logic is further configured to: control the multiplexer to select a second nanopore unit of the plurality of nanopore units, and configure the feedback circuit to provide a second amount of feedback for the second nanopore unit.

In some aspects, the techniques described herein relate to a system, wherein the second amount of feedback differs from the first amount of feedback.

In some aspects, the techniques described herein relate to a system, further including memory coupled to the control logic, and wherein the control logic is further configured to: retrieve first information from the memory, the first information associated with a prior configuration of the feedback circuit for the first nanopore unit, and retrieve second information from the memory, the second information associated with a prior configuration of the feedback circuit for the second nanopore unit.

In some aspects, the techniques described herein relate to a system, further including tuning logic coupled to the feedback circuit, wherein the tuning logic is configured to: adjust at least one parameter of the feedback circuit to increase or decrease the first amount of feedback, and/or adjust the at least one parameter of the feedback circuit to increase or decrease the second amount of feedback.

In some aspects, the techniques described herein relate to a system, further including tuning logic coupled to the feedback circuit, wherein the tuning logic is configured to: adjust at least one parameter of the feedback circuit to provide a same amount of feedback for the first nanopore unit and the second nanopore unit.

In some aspects, the techniques described herein relate to a system, further including tuning logic coupled to the feedback circuit, wherein the tuning logic is configured to: adjust at least one parameter of the feedback circuit to provide a customized amount of feedback depending on an identity of a nanopore unit selected by the multiplexer.

In some aspects, the techniques described herein relate to a system, wherein the first amount of feedback is equal to the second amount of feedback.

In some aspects, the techniques described herein relate to a system, wherein in the first amount of feedback and the second amount of feedback are different.

In some aspects, the techniques described herein relate to a method of reducing noise in a nanopore signal at an input of an amplifier, the method including: applying a voltage to a nanopore to produce the nanopore signal at the input of the amplifier; configuring an aspect of a feedback circuit coupled to and situated between an output of the amplifier and the input of the amplifier; detecting a characteristic of an amplifier output signal; adjusting the aspect of the feedback circuit in response to the detected characteristic of the amplifier output signal; and the feedback circuit injecting a feedback signal at the input of the amplifier.

In some aspects, the techniques described herein relate to a method, wherein the aspect of the feedback circuit is a capacitance.

In some aspects, the techniques described herein relate to a method, wherein the characteristic of the amplifier output signal is a signal-to-noise ratio.

In some aspects, the techniques described herein relate to a method, wherein detecting the characteristic of the amplifier output signal includes processing a digitized version of the amplifier output signal.

In some aspects, the techniques described herein relate to a method, wherein the characteristic of the amplifier output signal includes an error rate associated with an error correcting code protecting data represented by the nanopore signal.

In some aspects, the techniques described herein relate to a method, wherein detecting the characteristic of the amplifier output signal includes a downstream process or component determining the characteristic of the amplifier output signal.

In some aspects, the techniques described herein relate to a method, wherein the characteristic of the amplifier output signal is a stability.

In some aspects, the techniques described herein relate to a method, wherein the characteristic of the amplifier output signal is an amount of oscillation.

In some aspects, the techniques described herein relate to a method, wherein the characteristic of the amplifier output signal is a stability, and wherein adjusting the aspect of the feedback circuit in response to the detected characteristic of the amplifier output signal includes: adjusting the aspect of the feedback circuit to increase an amount of feedback provided at the input of the amplifier; detecting an onset of instability in the amplifier output signal after adjusting the aspect of the feedback circuit to increase the amount of feedback provided at the input of the amplifier; and in response to detecting the onset of instability in the amplifier output signal, adjusting the aspect of the feedback circuit to decrease the amount of feedback provided at the input of the amplifier.

In some aspects, the techniques described herein relate to a method, wherein detecting the onset of instability in the amplifier output signal includes detecting oscillations in the amplifier output signal.

In some aspects, the techniques described herein relate to a method, further including: determining an optimized aspect of the feedback circuit by iteratively (a) detecting the characteristic of the amplifier output signal, and (b) adjusting the aspect of the feedback circuit in response to the detected characteristic of the amplifier output signal.

In some aspects, the techniques described herein relate to a method, further including: storing information identifying the optimized aspect of the feedback circuit in memory.

In some aspects, the techniques described herein relate to a method, further including: retrieving the information identifying the optimized aspect of the feedback circuit from the memory, and wherein configuring the aspect of the feedback circuit includes configuring the aspect in accordance with the information identifying the optimized aspect of the feedback circuit.

In some aspects, the techniques described herein relate to a system for detecting molecules, the system including: a nanopore unit including a nanopore, a sense electrode, and a counter electrode; an amplifier; and a bootstrap circuit, wherein: the sense electrode is configured to: in cooperation with the counter electrode, detect a current associated with the nanopore, and provide the detected current to an input of the amplifier, the amplifier is configured to provide, at an output of the amplifier, a signal representing the detected current, and the bootstrap circuit is coupled to and situated between (a) the output of the amplifier and the counter electrode, or (b) the sense electrode and the counter electrode.

In some aspects, the techniques described herein relate to a system, wherein the bootstrap circuit is frequency-selective.

In some aspects, the techniques described herein relate to a system, wherein the bootstrap circuit includes at least one resistor and at least one capacitor.

In some aspects, the techniques described herein relate to a system, wherein the bootstrap circuit is configured to provide (i) a high-frequency voltage component to mitigate an effect of a parasitic capacitance between the sense electrode and the counter electrode, and (ii) a low-frequency voltage component to bias the counter electrode.

In some aspects, the techniques described herein relate to a system, wherein the bootstrap circuit includes a transistor and a capacitor.

In some aspects, the techniques described herein relate to a system, wherein the transistor is a source follower or an emitter follower.

In some aspects, the techniques described herein relate to a system, wherein the transistor is a bipolar junction transistor (BJT) or a junction-gate field effect transistor (JFET).

In some aspects, the techniques described herein relate to a system, wherein the bootstrap circuit includes an amplifier.

In some aspects, the techniques described herein relate to a system for detecting molecules, the system including: a plurality of nanopores; a plurality of sense electrodes, each of the plurality of sense electrodes associated with a respective one of the plurality of nanopores; a counter electrode shared by the plurality of nanopores; a multiplexer coupled to the plurality of sense electrodes and configured to select one of the plurality of sense electrodes to read an associated one of the plurality of nanopores; a read circuit coupled to the multiplexer and configured to receive, from the multiplexer, a signal from the selected one of the plurality of sense electrodes; a bootstrap circuit coupled to the counter electrode; a bias circuit coupled to the counter electrode; a digitizer coupled to an output of the read circuit; and control logic coupled to the digitizer.

In some aspects, the techniques described herein relate to a system, wherein the bootstrap circuit is frequency-selective.

In some aspects, the techniques described herein relate to a system, wherein the bootstrap circuit includes at least one resistor and at least one capacitor.

In some aspects, the techniques described herein relate to a system, wherein the bootstrap circuit is configured to provide (i) a high-frequency voltage component to mitigate an effect of a parasitic capacitance between the selected one of the plurality of sense electrodes and the counter electrode, and (ii) a low-frequency voltage component to bias the counter electrode.

In some aspects, the techniques described herein relate to a system, wherein the bootstrap circuit includes a transistor and a capacitor.

In some aspects, the techniques described herein relate to a system, wherein the transistor is a source follower or an emitter follower.

In some aspects, the techniques described herein relate to a system, wherein the transistor is a bipolar junction transistor (BJT) or a junction-gate field effect transistor (JFET).

In some aspects, the techniques described herein relate to a system, wherein the bootstrap circuit includes an amplifier.

In some aspects, the techniques described herein relate to a system, wherein an input of the bootstrap circuit is from (a) an output of the read circuit, or (b) the selected one of the plurality of sense electrodes.

In some aspects, the techniques described herein relate to a system, wherein the plurality of nanopores is a first plurality of nanopores, the plurality of sense electrodes is a first plurality of sense electrodes, the counter electrode is a first counter electrode, the multiplexer is a first multiplexer, the read circuit is a first read circuit, the bootstrap circuit is a first bootstrap circuit, and the bias circuit is a first bias circuit, and further including: a second plurality of nanopores; a second plurality of sense electrodes, each of the second plurality of sense electrodes associated with a respective one of the second plurality of nanopores; a second counter electrode shared by the second plurality of nanopores; a second multiplexer coupled to the second plurality of sense electrodes and configured to select one of the second plurality of sense electrodes to read an associated one of the second plurality of nanopores; a second read circuit coupled to the second multiplexer and configured to receive, from the second multiplexer, a signal from the selected one of the second plurality of sense electrodes; a second bootstrap circuit coupled to the second counter electrode; a second bias circuit coupled to the second counter electrode; and a read multiplexer coupled to an output of the first read circuit and an output of the second read circuit and configured to provide a signal to the digitizer, and wherein the control logic further coupled to the first multiplexer and the second multiplexer and is configured to control the first multiplexer and the second multiplexer to select a single nanopore from among the first plurality of nanopores and the second plurality of nanopores.

In some aspects, the techniques described herein relate to a system, wherein: an input of the first bootstrap circuit is from (a) an output of the first read circuit, or (b) the selected one of the first plurality of sense electrodes, and an input of the second bootstrap circuit is from (i) an output of the second read circuit, or (ii) the selected one of the second plurality of sense electrodes.

BRIEF DESCRIPTION OF THE DRAWINGS

Objects, features, and advantages of the disclosure will be readily apparent from the following description of certain embodiments taken in conjunction with the accompanying drawings in which.

Figure 1:
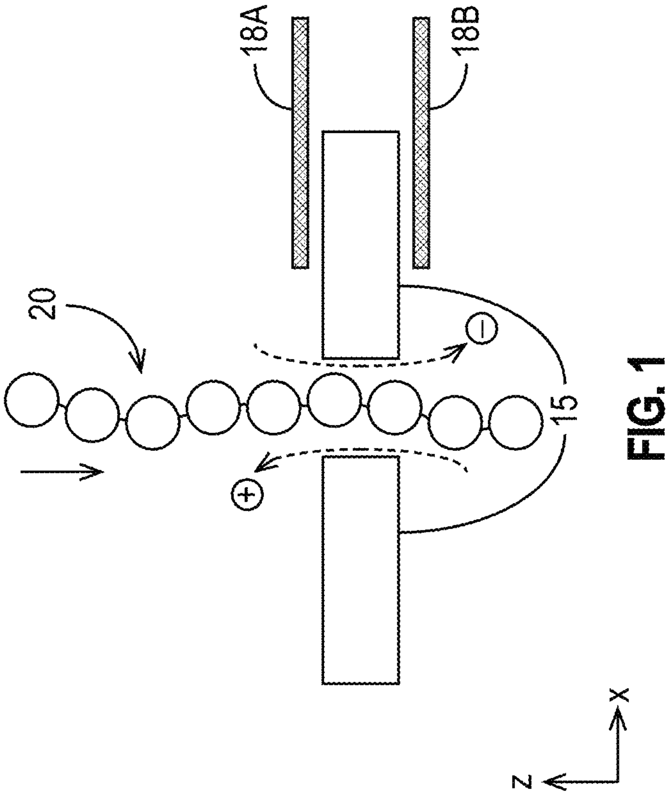
FIG. 1 illustrates a nanopore with a molecule passing through it in accordance with some embodiments.

To facilitate understanding, identical reference numerals have been used, where possible, to designate identical elements that are common to the figures. It is contemplated that elements disclosed in one embodiment may be beneficially utilized in other embodiments without specific recitation. Moreover, the description of an element in the context of one drawing is applicable to other drawings illustrating that element.

DETAILED DESCRIPTION

Disclosed herein are low-noise readout circuits, devices, and systems, and methods of using them. The disclosed circuits can substantially reduce amplifier input current noise.

FIG. 1 illustrates a nanopore 15 with a molecule 20 (e.g., a single-stranded DNA (ssDNA) molecule), passing through it. Two electrodes, which are referred to herein as the sense electrode 18A and the counter electrode 18B, are situated near the nanopore 15 to sense the ionic or tunnel current through the nanopore 15. The sense electrode 18A and/or counter electrode 18B are typically connected to a voltage source (not illustrated), which creates a potential between the sense electrode 18A and counter electrode 18B.

Figure 2:
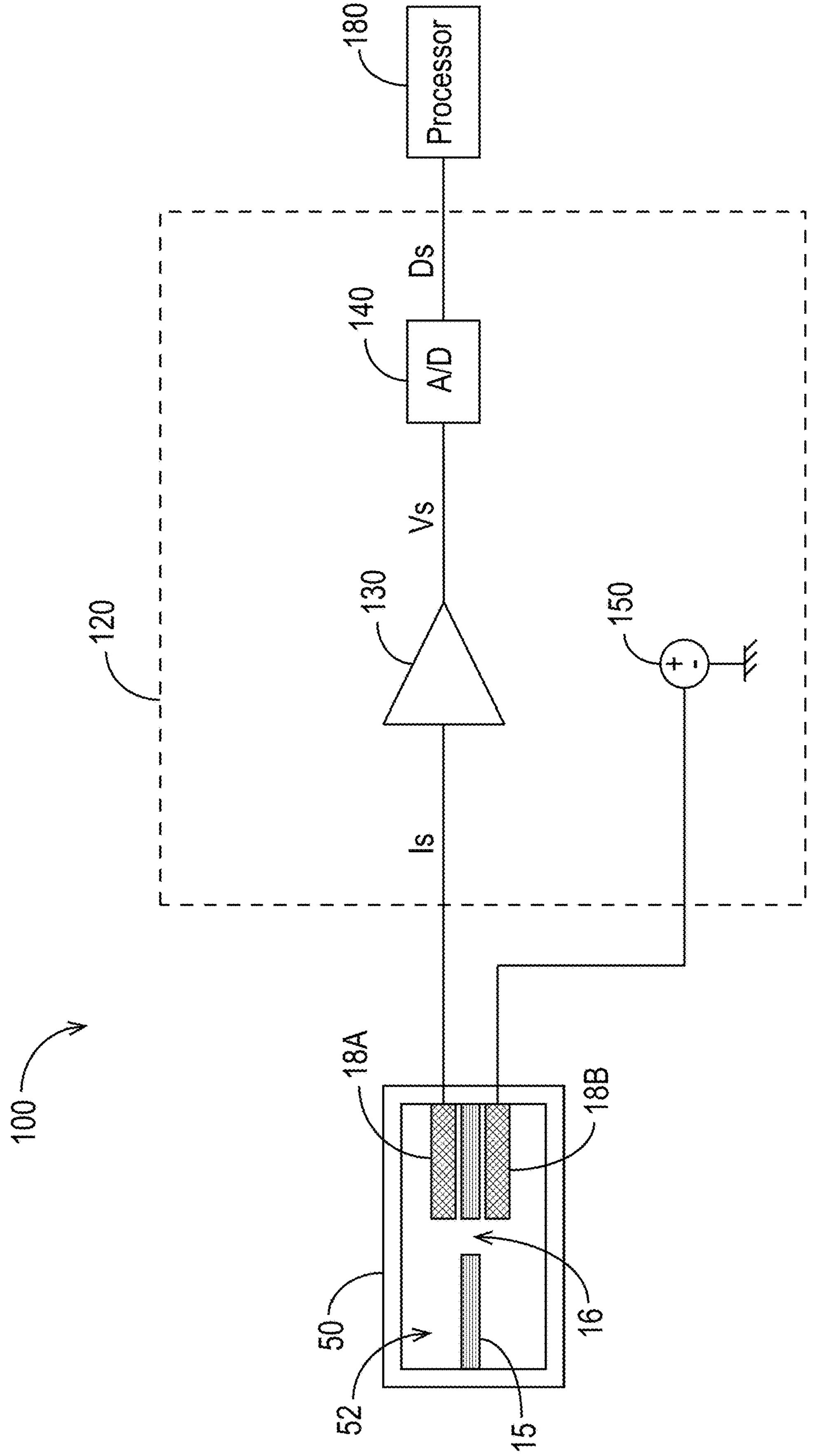
FIG. 2 is a diagram of a system for detecting molecules in accordance with some embodiments.

FIG. 2 is a diagram of a system 100 for detecting molecules in accordance with some embodiments. The system 100 includes a nanopore unit 50, a detection device 120, and a processing device 180. The illustrated nanopore unit 50 has a fluid chamber 52 that can be filled with an electrolyte solution containing molecules to be detected (e.g., molecule 20 from FIG. 1). The nanopore unit 50 includes a nanopore 15 with a hole 16. The sense electrode 18A and counter electrode 18B are situated on either side of the nanopore 15, as illustrated. As explained further below, the sense electrode 18A and/or counter electrode 18B may be in contact with the nanopore 15 or they may be separated from it.

In the diagram of FIG. 2, the detection device 120 comprises an amplifier 130, an analog-to-digital converter 140 (or, more generally, a digitizer), and a voltage source 150. The amplifier 130 may be, for example, a transimpedance amplifier that is configured to convert the detected current, Is, to a voltage, Vs. The analog-to-digital converter 140 is configured to digitize the output voltage, Vs, of the amplifier 130 and provide it to the processing device 180 (e.g., via an interface). The voltage source 150 is configured to generate a voltage of sufficient magnitude across the sense electrode 18A and counter electrode 18B to drive molecules within the fluid chamber 52 into the hole 16 and to allow the effect of the molecules on the current to be detected by the amplifier 130. The voltage source 150 may be capable of providing a variable voltage level Vb across the sense electrode 18A and counter electrode 18B. The amplifier 130 may operate by, for example, detecting the resistance between the sense electrode 18A and the counter electrode 18B when the voltage is applied by the voltage source 150.

In operation, the voltage source 150 generates a voltage across the sense electrode 18A and counter electrode 18B, which causes an ionic or tunnel current, Is, to flow between the sense electrode 18A and counter electrode 18B and also causes molecules in the fluid chamber 52 to be drawn into the hole 16 of the nanopore 15. If the voltage across the sense electrode 18A and counter electrode 18B is Vb, the current Is is given by Ohm's law: Is=Vb/Rp, where Rp is the resistance through the nanopore 15 encountered by a molecule 20 as it passes through the hole 16. The amplifier 130 converts the current Is to a voltage, Vs, which it passes to the analog-to-digital converter 140. The voltage Vs is dependent on the gain of the amplifier 130. The analog-to-digital converter 140 converts the voltage signal Vs into digital data Ds, which it passes to the processing device 180, which may be situated in a different (external) physical device than the nanopore unit 50 and/or detection device 120 (e.g., the nanopore unit 50 and/or detection device 120 may be situated on/in a single integrated circuit device, and the processing device 180 may be in a computer or other device external to the integrated circuit device). The analog-to-digital converter 140 may provide the sampled signal Ds to the processing device 180 using any available communication path (e.g., wired or wireless) and in accordance with any suitable protocol (e.g., IEEE 802.11, Ethernet, USB, etc.).

As described further below, multiple instantiations of the nanopore unit 50, the detection device 120, and/or the processing device 180 may be included in a single physical device, or they may be separate. For example, the nanopore unit 50 and the detection device 120 may be included in a single device that is connected to the processing device 180 (e.g., a computer or other processor). In addition, a system may include multiple nanopores 15 connected to sense electrodes 18A and counter electrodes 18B (which may be dedicated or shared), in turn coupled to detection devices 120 (which may be dedicated or shared) that measure the respective currents (Is).

Figure 3A:
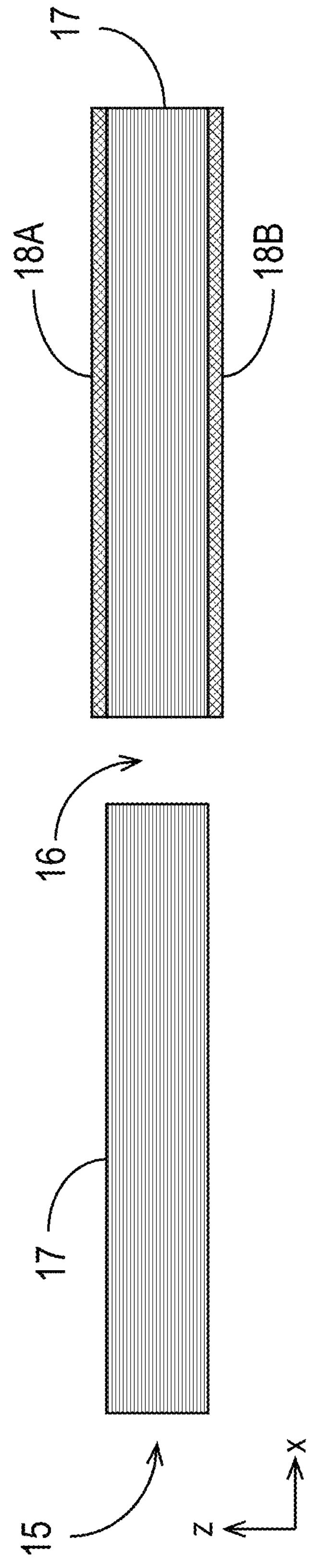
FIG. 3A illustrates a cross-section of an example configuration of a nanopore, a sense electrode, and a counter electrode in accordance with some embodiments.

FIG. 3A illustrates a cross-section of an example configuration of a nanopore 15 and the sense electrode 18A and counter electrode 18B in accordance with some embodiments. The cross-section is in the x-z plane, as indicated by the axes. As illustrated in the example of FIG. 3A, the nanopore 15 can comprise a thin dielectric layer 17 with a hole 16 and two electrodes, namely, the sense electrode 18A and counter electrode 18B, attached to the sides of the nanopore 15. The sense electrode 18A and counter electrode 18B may have thicknesses in the z-direction of, for example, around 10 nm.

Figure 3B:
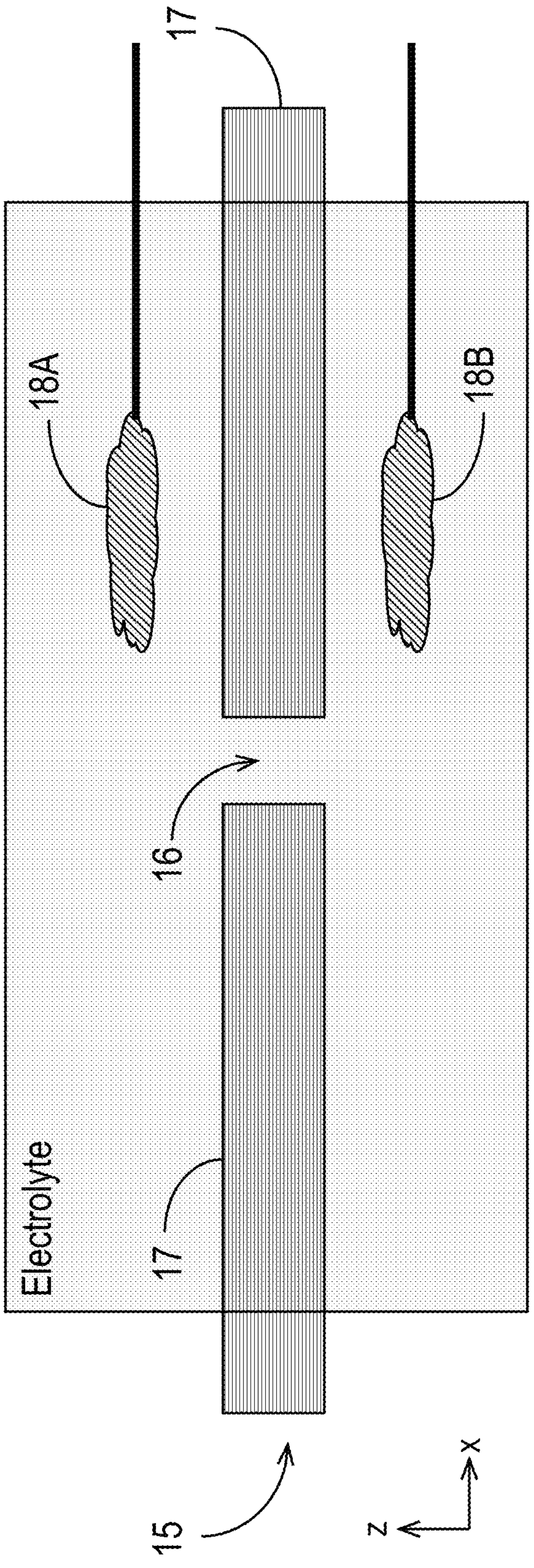
FIG. 3B illustrates a cross-section of an alternative example configuration of a nanopore, a sense electrode, and a counter electrode in accordance with some embodiments.

FIG. 3B illustrates a cross-section of an alternative example configuration of a nanopore 15 and the sense electrode 18A and counter electrode 18B in accordance with some embodiments. As illustrated in FIG. 3B, the sense electrode 18A and counter electrode 18B can be electrochemical electrodes, e.g. silver/silver-chloride pairs.

With either of the sense electrode 18A and counter electrode 18B embodiments illustrated in FIGS. 3A and 3B, the thin dielectric layer 17 of the nanopore 15 is very thin (e.g., in the nm range) to create a nanopore 15 with a suitable aspect ratio so that molecules passing through the hole 16 will cause measurable disturbances in the current. As a result, the capacitance between the sense electrode 18A and counter electrode 18B, which is inversely proportional to the thickness of the thin dielectric layer 17, is naturally very large. This capacitance can amplify the noise of the applied voltage Vb by forming a pole with the output impedance of the amplifier 130. It can also cause the detection device 120 to have an unstable dynamic response at higher frequencies. This instability can reduce the usefulness of the system 100 by preventing it from being able to detect rapid changes in the current as molecules pass through the nanopore 15 at the applied voltage Vb. Specifically, the capacitance amplifies the noise voltage, particularly at higher frequencies. The amplified noise limits the frequency at which the nanopore 15 can read or detect molecules passing through its hole 16.

Figure 4:
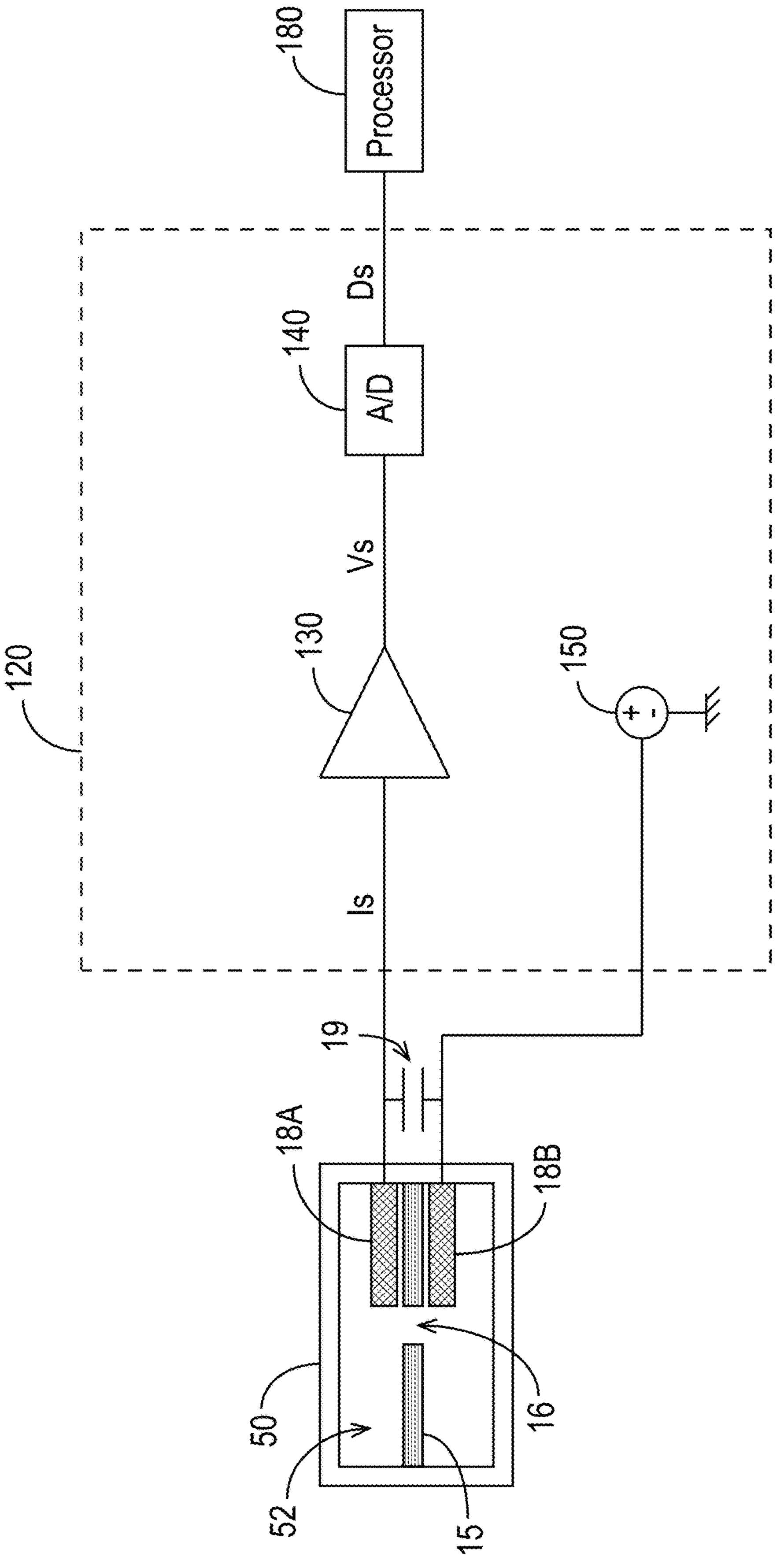
FIG. 4 is a conceptual illustration of the system of FIG. 2 with the parasitic capacitance between the sense electrode and the counter electrode represented as a capacitor in accordance with some embodiments.

The capacitance of the nanopore 15 can be modeled as the parallel-plate capacitance of the constituent elements of the nanopore unit 50. FIG. 4 is a conceptual illustration of the system 100 of FIG. 2 representing the capacitance between the sense electrode 18A and the counter electrode 18B as a capacitor. As illustrated in FIG. 4, the capacitance can be considered as a parasitic capacitance 19 between the sense electrode 18A and counter electrode 18B. The parasitic capacitance 19 acts as a charge sink for the sense electrode 18A and can create a peak in the noise spectrum. For example, if a potential difference ΔU is created between the sense electrode 18A and counter electrode 18B, a charge Q=ΔU*C flows into the parasitic capacitance 19, which reduces the signal (e.g., the current Is) that is sensed by the amplifier 130 and, correspondingly, reduces the SNR of the measurement.

Prior approaches to improving the SNR have included reducing the capacitance of the nanopore 15 by modifying its physical layout, reducing the bandwidth of the amplifier 130, and reducing the translocation speed of the molecules passing through the nanopore 15. All of these approaches have drawbacks. For example, changes to the physical layout are limited by manufacturability, and reduced amplifier 130 bandwidth and/or translocation speed of molecules through the nanopore 15 reduces the rate at which molecules can be read. Therefore, there remains a need for additional solutions.

Disclosed herein are devices, systems, and methods that can improve the SNR of nanopore 15 measurements by mitigating the effect of the parasitic capacitance 19. In some embodiments, a feedback circuit is used to inject a charge into the sense electrode 18A to at least partially cancel the parasitic capacitance between the sense electrode 18A and the counter electrode 18B. In some embodiments, bootstrapping of a signal from the amplifier 130 output or from the sense electrode 18A is used to inject a charge on the counter electrode 18B to substantially cancel the parasitic capacitance 19.

Each of these approaches is discussed further below.

Feedback into Sense Electrode

In some embodiments, a feedback circuit is used to inject a charge into the sense electrode 18A to cancel at least part of the parasitic capacitance 19. Ideally, the amount of charge injected corresponds exactly to the charge that would otherwise be diverted to the parasitic capacitance 19. In some embodiments, slightly less charge is injected to maintain stable operating conditions.

Figure 5:
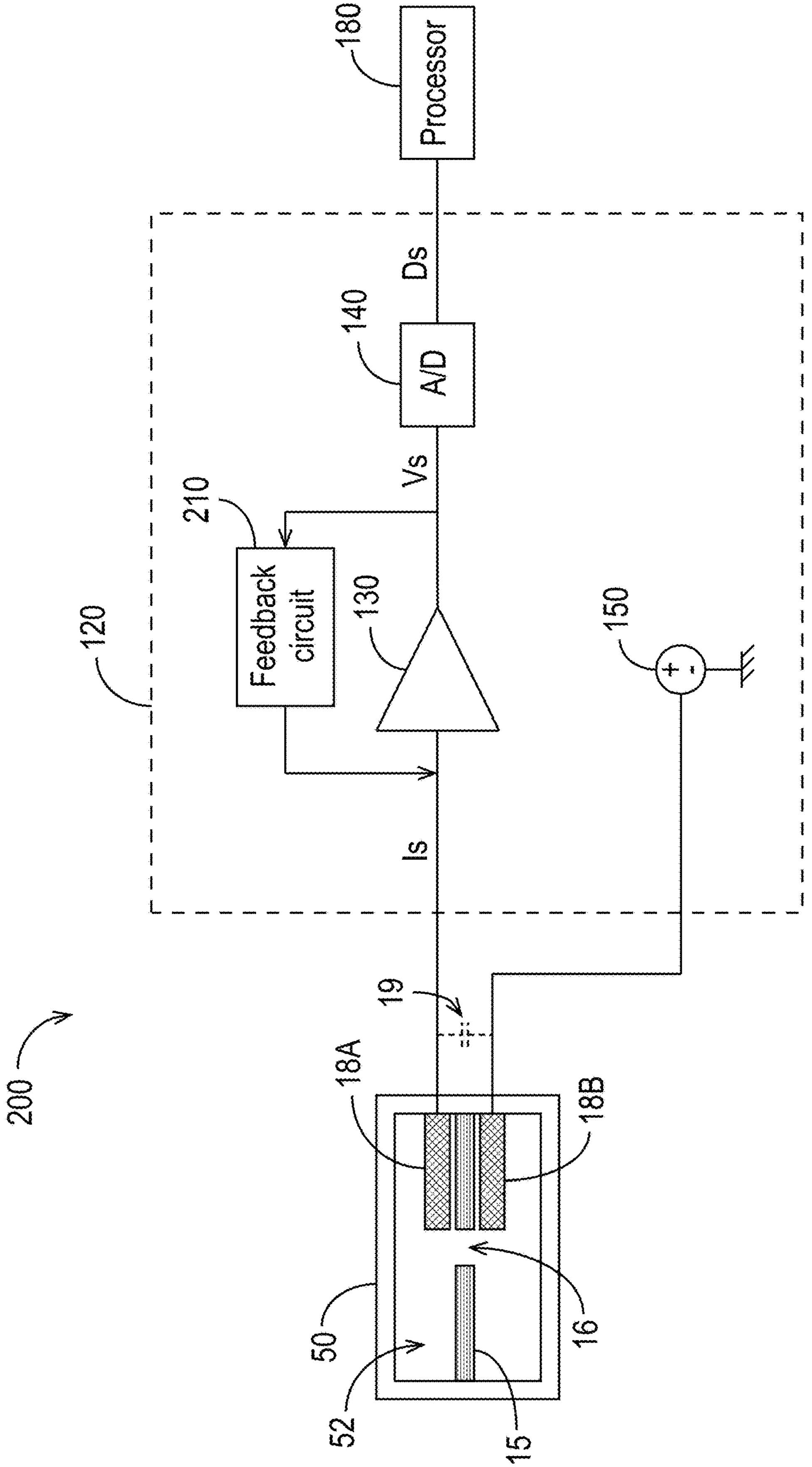
FIG. 5 is a diagram illustrating an example system in accordance with some embodiments.

FIG. 5 is a diagram illustrating an example system 200 in accordance with some embodiments. As shown in FIG. 5, the current detected by the sense electrode 18A is measured by the amplifier 130, which may be a low-input-capacitance (high-impedance) buffer amplifier. A feedback circuit 210 feeds the output of the amplifier 130 back to the sense electrode 18A. If the voltage on the sense electrode 18A changes by ΔU, a charge proportional to this change in voltage is injected back into the input of the amplifier 130. This injected charge effectively cancels at least a portion the parasitic capacitance 19 between the sense electrode 18A and the counter electrode 18B (illustrated by the parasitic capacitance 19 having a smaller size and being shown in dashed lines in FIG. 5).

For large charge feedback, the system 200 may become unstable, so in practice, it is likely that the feedback circuit 210 will inject slightly less than Q=ΔU*C to maintain stability. In some embodiments, the feedback circuit 210 is tuned such that the feedback is adjusted (e.g., increased) until oscillations are detected in the output signal (Vs) from the amplifier 130, at which point the feedback is decreased slightly. Thus, the feedback circuit 210 can provide near-optimal feedback to substantially cancel the parasitic capacitance 19 between the sense electrode 18A and counter electrode 18B.

There are a number of ways to inject the charge (feedback) onto the sense electrode 18A. For example, the feedback circuit 210 can comprise a buffer amplifier (e.g., an amplifier that transforms the electrical impedance from one circuit to another to try to prevent the signal source from being affected by whatever currents (or voltages) the load may be produced with). As another example, the feedback circuit 210 can comprise a charge amplifier (e.g., an electronic current integrator the produces a voltage output proportional to the total charge injected). As will be appreciated by those having ordinary skill in the art, the charge amplifier uses a feedback reference capacitor to offset the input current. It produces an output voltage that is inversely proportional to the value of the reference capacitor and proportional to the total input charge flowing during a time period, thereby acting as a charge-to-voltage converter with a gain that is dependent on the capacitance of the feedback capacitor. Using a charge amplifier in the feedback circuit 210 can virtually ground the parasitic capacitance 19 between the sense electrode 18A and counter electrode 18B, which substantially removes its influence from the output of the amplifier 130.

The buffer amplifier and charge amplifier described above are examples of components that can be included in the feedback circuit 210. As will be appreciated by those having ordinary skill in the art, other circuits, components, and approaches instead of or in addition to the examples given herein are possible, are contemplated, and are within the scope of the disclosures herein. For example, the feedback circuit 210 may comprise an AC-coupled amplifier. Those having ordinary skill in the art will understand how to design the feedback circuit 210 to provide a feedback signal that substantially cancels the charge that would otherwise be diverted from the sense electrode 18A (and, therefore, the amplifier 130 input) by the parasitic capacitance 19 between the sense electrode 18A and the counter electrode 18B.

As will be appreciated, the feedback circuit 210 illustrated in FIG. 5 may include any suitable components. For example, the feedback circuit 210 may include a feedback capacitor, which, in some embodiments, is integrated into the nanopore unit 50. Integrating a feedback capacitor near the sense electrode 18A can be advantageous because it can provide additional shielding of the sense electrode 18A.

Figure 6A:
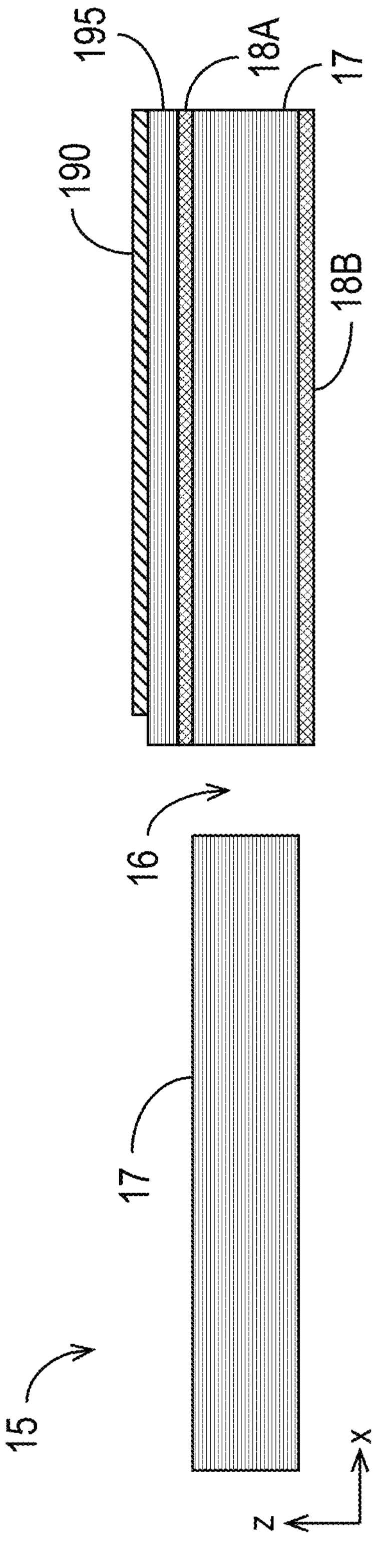
FIG. 6A illustrates an example integrated feedback capacitor in accordance with some embodiments.

FIG. 6A illustrates an example integrated feedback capacitor in accordance with some embodiments. As shown, a layer of feedback capacitor dielectric 195 is deposited over the sense electrode 18A, and a feedback electrode 190 is deposited over the feedback capacitor dielectric 195. The feedback capacitor dielectric 195 may comprise any suitable dielectric. Examples include, but are not limited to, $SiO_2$, $Al_2O_3$, glass, polymers, organosilicate glass, or any other suitable dielectric. The feedback electrode 190 may comprise, for example, a conductor (e.g., Ti, Ag, Al, W, Pt, Cu, TiN, polysilicon, doped semiconductors, a two-dimensional material such as graphene, etc.). The feedback electrode 190 may have any suitable dimensions, which will depend on a variety of factors, as will be appreciated by those having ordinary skill in the art.

In the example illustrated in FIG. 6A, the feedback electrode 190 is recessed from the hole 16. It will be appreciated from the disclosures herein that recessing the feedback electrode 190 from the hole 16 can reduce or prevent interference with the current detection by the sense electrode 18A and the counter electrode 18B and/or a short circuit. It is to be appreciated, however, that in some embodiments, the feedback electrode 190 might not be recessed from the hole 16. The feedback electrode 190 forms a feedback capacitor with the sense electrode 18A as the other terminal of the feedback capacitor. The feedback electrode 190 is coupled to the output of the amplifier 130. A potential benefit of the arrangement of FIG. 6A is better shielding of the sense electrode 18A from electrolyte within the fluid chamber 52 of the nanopore unit 50.

Figure 6B:
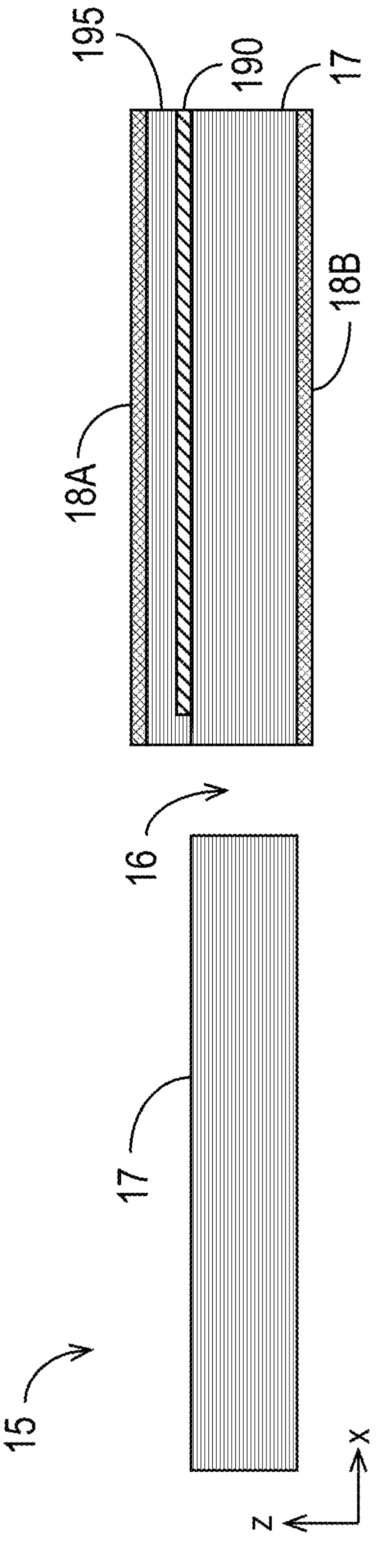
FIG. 6B illustrates another example integrated capacitor in accordance with some embodiments.

FIG. 6B illustrates another example integrated capacitor in accordance with some embodiments. As shown, in this example, the feedback electrode 190 is deposited over the thin dielectric layer 17 of the nanopore 15. The feedback capacitor dielectric 195 is deposited over the feedback electrode 190, and the sense electrode 18A is deposited over the feedback capacitor dielectric 195. In the example illustrated in FIG. 6B, the feedback electrode 190 is recessed from the hole 16. The feedback electrode 190 is coupled to the output of the amplifier 130. In this configuration, the sense electrode 18A and feedback electrode 190 are the terminals of the feedback capacitor. A potential benefit of the arrangement of FIG. 6B is improved shielding from the counter electrode 18B and improved reduction of the parasitic capacitance 19.

Figure 7:
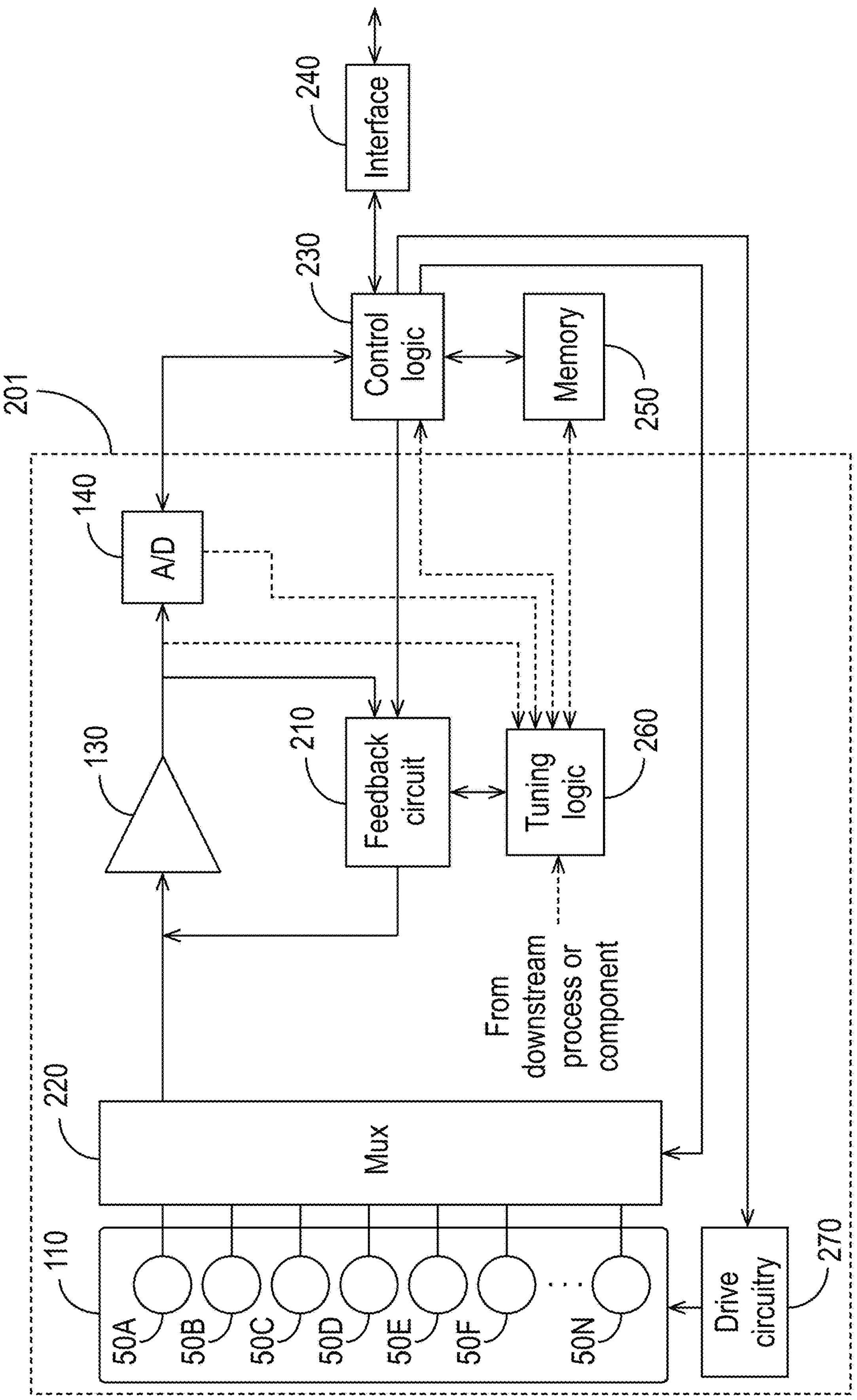
FIG. 7 illustrates an example of a system that includes a feedback circuit in accordance with some embodiments.

FIG. 7 illustrates an example of a system 201 that includes a feedback circuit 210 in accordance with some embodiments. In the illustrated example, the system 201 comprises an array 110 of nanopore units 50. In FIG. 7, the array 110 is shown as including at least the nanopore unit 50A, the nanopore unit 50B, the nanopore unit 50C, the nanopore unit 50D, the nanopore unit 50E, the nanopore unit 50F, and the nanopore unit 50N, but it is to be appreciated that the array 110 can include fewer or more nanopore units 50 than shown. Moreover, the use of the letter "N" in the last illustrated nanopore unit 50 is not intended to suggest that the array 110 of the system 201 includes any particular number of nanopore units 50. In general, the array 110 can include any number of nanopore units 50 (e.g., one or more).

The array 110 is coupled to a multiplexer 220. As shown in FIG. 7, the multiplexer 220 has a plurality of inputs, each corresponding to a respective one of the nanopore units 50 in the array 110, and a single output. The multiplexer 220 may be, for example, configured to cycle through individual nanopore units 50 of the array 110 to read each of the nanopores 15 in a systematic way (e.g., periodically, in accordance with a clock signal, in response to an instruction from the control logic 230 discussed below, etc.). Alternatively or in addition, the multiplexer 220 may be configured to select any one nanopore unit 50 in the array 110 at any time (e.g., when desirable or necessary) and to read its nanopore 15 (e.g., provide a signal representing its current to the amplifier 130). Accordingly, as illustrated in FIG. 7, in the system 201, a plurality (some or all) of the nanopore units 50 in the array 110 are coupled to the multiplexer 220.

As shown in the example of FIG. 7, the multiplexer 220 is coupled to and provides a signal corresponding to a selected nanopore unit 50 to the amplifier 130. Referring back to FIG. 2, the multiplexer 220 may provide the current Is corresponding to the selected nanopore 15 to the amplifier 130. As illustrated in FIG. 7, the amplifier 130 of the system 201 provides an output signal (e.g., Vs of FIG. 2) to the analog-to-digital converter 140 (or, generally, a digitizer). The analog-to-digital converter 140 is coupled to, and can provide signals to and receive signals from, control logic 230. The control logic 230 is coupled to memory 250 and to an interface 240. The memory may be on-board (e.g., on an integrated circuit chip that includes some or all components of the system 201, etc.), or it may be external memory. The interface 240 may couple the system 201 to a processing device (e.g., the processing device 180 shown in FIG. 2).

The system 201 shown in FIG. 7 also includes a feedback circuit 210. The feedback circuit 210 is coupled to the input of the amplifier 130 to inject a feedback signal (e.g., as described above in the discussion of FIG. 5). As shown in FIG. 7, the feedback circuit 210 may obtain one or more inputs from one or more sources. For example, the feedback circuit 210 may be coupled to the output of the amplifier 130, in which case the feedback circuit 210 obtains an analog signal (the analog output) from the amplifier 130. Alternatively, or in addition, the feedback circuit 210 may be coupled to and may obtain a signal (e.g., a digital signal) from the control logic 230. The control logic 230 may provide, for example, the digital output from the analog-to-digital converter 140 and/or feedback parameters or information that may have been previously stored (e.g., concerning how the feedback circuit 210 should be configured).

As shown in FIG. 7, the control logic 230 is coupled to memory 250, which may store information that can be used by or to configure the feedback circuit 210. For example, memory 250, which may be on-chip or off-chip memory, can store previously-determined feedback information or parameters for one or more nanopore units 50 of the array 110. The memory 250 may store information or parameters that apply to multiple nanopore units 50 of the array 110, or the memory 250 may store information for individual nanopore units 50 of the array 110. As a specific example, when the system 201 is first placed into use, the control logic 230 can route the digital output from the analog-to-digital converter 140 to the feedback circuit 210, which can then adjust its output signal to provide an appropriate amount of feedback to the amplifier 130. Once the feedback circuit 210 (e.g., in cooperation with the tuning logic 260 discussed further below) has determined the appropriate amount of feedback, the control logic 230 may obtain information about the configuration that resulted in the appropriate amount of feedback, which it may store in memory 250. At a later time, the control logic 230 may retrieve the configuration information (e.g., feedback-related parameters such as signal level, voltage or gain settings, etc.) and provide it to the feedback circuit 210. The feedback circuit 210 can then implement the configuration to provide the appropriate feedback at the input to the amplifier 130.

The control logic 230 is also coupled to and configured to provide signals/instructions to the drive circuitry 270. The drive circuitry 270 is coupled to the array 110 and, as its name suggests, is the driver for at least one nanopore unit 50 of the array 110. For example, the drive circuitry 270 may include the voltage source 150 illustrated in FIG. 2. The drive circuitry 270 is the power supply that biases the array 110, and it includes at least one drive circuit coupled to at least one nanopore unit 50.

The control logic 230 is also coupled to and configured to provide signals/instructions to the multiplexer 220. For example, the control logic 230 can provide a signal to cause the multiplexer 220 to cycle through the connected nanopore units 50 to allow the nanopore 15 currents to be read/measured. Alternatively or in addition, the control logic 230 can select a particular nanopore unit 50 connected to the multiplexer 220 by providing a signal to the multiplexer 220.

The example system 201 illustrated in FIG. 7 also includes optional tuning logic 260. The tuning logic 260 may be included to assist the feedback circuit 210 in providing the appropriate feedback signal at the input to the amplifier 130. The tuning logic 260 may be configured to (a) adjust a parameter (e.g., a capacitance) of the feedback circuit 210 to increase an amount of feedback provided by the feedback circuit 210, monitor the signal representing the current (e.g., directly or via receipt of a signal or indicator from another component), in response to an indication that a signal quality associated with the signal representing the detected current is improving, adjust the parameter to increase the amount of feedback provided by the feedback circuit, and in response to detecting the onset of instability (e.g., oscillations or any other indication of instability, such as a bit error ratio) in the signal representing the current, adjust the parameter to decrease the amount of feedback provided by the feedback circuit 210. Optionally, the tuning logic 260 may store a value of the parameter after adjusting it (e.g., the tuned value of the parameter). The tuning logic 260 may iteratively adjust the feedback circuit 210 by making small adjustments and then detecting or monitoring their effect before deciding whether and what additional adjustments to make. The tuning logic 260 may be coupled to a memory and may be configured store information that identifies some optimized aspect of the feedback circuit 210 (e.g., a value of the parameter after finding a suitable parameter setting (or parameter settings) for the feedback circuit 210). The tuning logic 260 may be capable of tuning the feedback circuit 210 for each individual nanopore unit 50 so as to customize the amount of feedback provided by the feedback circuit 210 for each nanopore unit 50, or the tuning logic 260 may perform a tuning procedure that results in a feedback circuit 210 setting or settings that apply to more than one nanopore unit 50.

As illustrated in FIG. 7, the tuning logic 260 may be coupled to and receive information from and/or provide information to a number of the other components of the system 201 or external to the system 201. For example, the tuning logic 260 may have access to the raw analog output signal of the amplifier 130, the digitized output signal from the analog-to-digital converter 140, or the signal provided by the control logic 230 to the feedback circuit 210. In addition, or alternatively, the tuning logic 260 may have access to performance metrics and/or other information about the performance of the system 201 (e.g., proxies for SNR), such as, for example, when an error correction code (ECC) protects data represented by the nanopore 15 signal, ECC outputs, which can tell the tuning logic 260 whether the amount of feedback being provided by the feedback circuit 210 is adequate or inadequate. The tuning logic 260 can use the signals, metrics, and/or information available to it to determine what changes to the feedback signal might be warranted. For example, if the tuning logic 260 has access to the analog signal at the output of the amplifier 130 or the digitized version from the analog-to-digital converter 140, it can determine whether the output signal is oscillating, which would mean the system 201 is becoming unstable. In this case, the tuning logic 260 could adjust the feedback circuit 210 to reduce the amount of feedback being injected. As another example, if the tuning logic 260 has access to metrics from a downstream ECC, and the ECC output indicates an increase in detected errors (e.g., the bit error ratio) after the feedback circuit 210 has increased the amount of feedback (e.g., quantity of charge) being provided at the input to the amplifier 130, the tuning logic 260 might conclude that the amplitude of the feedback signal should be reduced. In addition, or alternatively, the tuning logic 260 may have access to quality-revealing information or metrics from downstream user-level software (e.g., that processes the information from the interface 240 and, for example, indicates whether an ongoing molecule detection is yielding expected results or garbage). The tuning logic 260 may be capable of providing information or instructions to other portions of the system 201. For example, the tuning logic 260 may provide information or instructions to the control logic 230, the memory 250, and/or the feedback circuit 210.

It is to be appreciated that the control logic 230, memory 250, and interface 240 are illustrated in FIG. 7 as external to the system 201, but this demarcation is solely for convenience of description. For example, FIG. 8, described below, includes multiple instantiations of the components of the system 201 shown in FIG. 7, as well as control logic and an interface. It is to be appreciated that the system 201 can include components or elements not illustrated in FIG. 7 as being part of the system 201. For example, the system 201 can include control logic 230, an interface 240, and/or memory 250.

Figure 8:
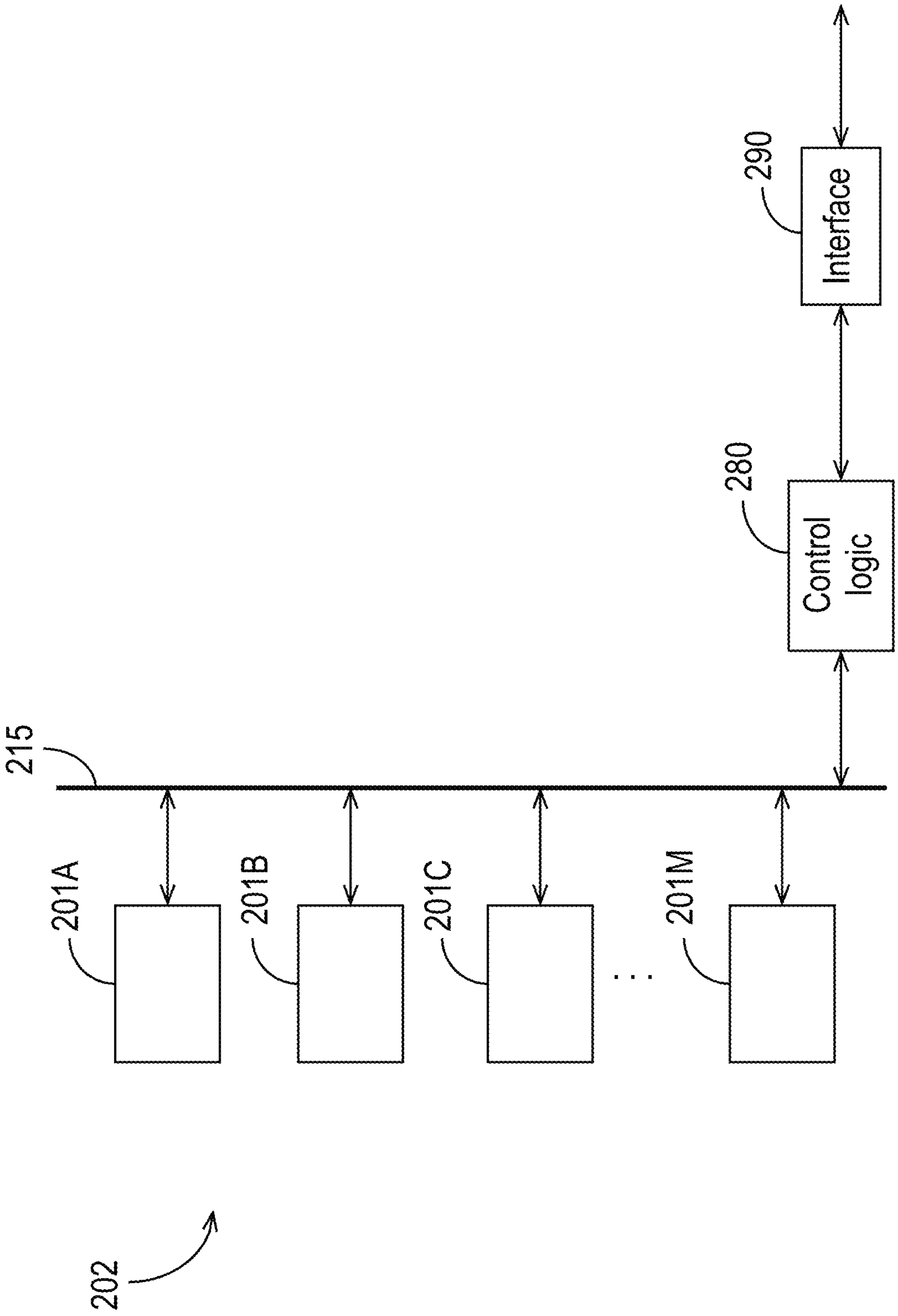
FIG. 8 illustrates another example of a system in accordance with some embodiments.

FIG. 8 illustrates another example of a system 202 in accordance with some embodiments. As illustrated, the system 202 includes one or more of the system 201 described above, thereby making them subsystems of the system 202. In the example shown in FIG. 8, the system 202 includes a plurality of systems 201 as subsystems. FIG. 8 illustrates and labels the subsystem 201A, the subsystem 201B, the subsystem 201C, and the subsystem 201M, but it is to be appreciated that the system 202 can include any number of systems 201 as subsystems. Moreover, the use of the letter "M" in the last illustrated system 201 is not intended to suggest that the system 202 includes any particular number of instances of systems 201 as subsystems.

The subsystem 201A, subsystem 201B, subsystem 201C, . . . , subsystem 201M (collectively referred to as the "subsystems 201*x*") of FIG. 8 are coupled to a bus 215. The bus 215 may be any suitable wired or wireless communication channel that allows the subsystems 201*x* in the system 202 to communicate with the control logic 280. The control logic 280 is configured to provide instructions/commands to and receive information/data from the subsystems 201*x*. The control logic 280 may be configured to perform the functions of the control logic 230 shown in FIG. 7, but for all of the subsystems 201*x* of the system 202. The control logic 280 is also coupled to an interface 290, which is configured to provide information to and obtain information from the control logic 280. The interface 290 may be any suitable interface and may communicate, wirelessly and/or via a wired communication path, with downstream components (e.g., processor, memory) using any suitable protocol. For example, it may provide communication via Wi-Fi, Ethernet, USB, etc. The interface 290 may be configured to perform the functions of the interface 240 shown in FIG. 7. The system 202 may also include memory (not illustrated), which may serve the same purpose(s) as described above for the memory 250 of FIG. 7.

Figure 9:
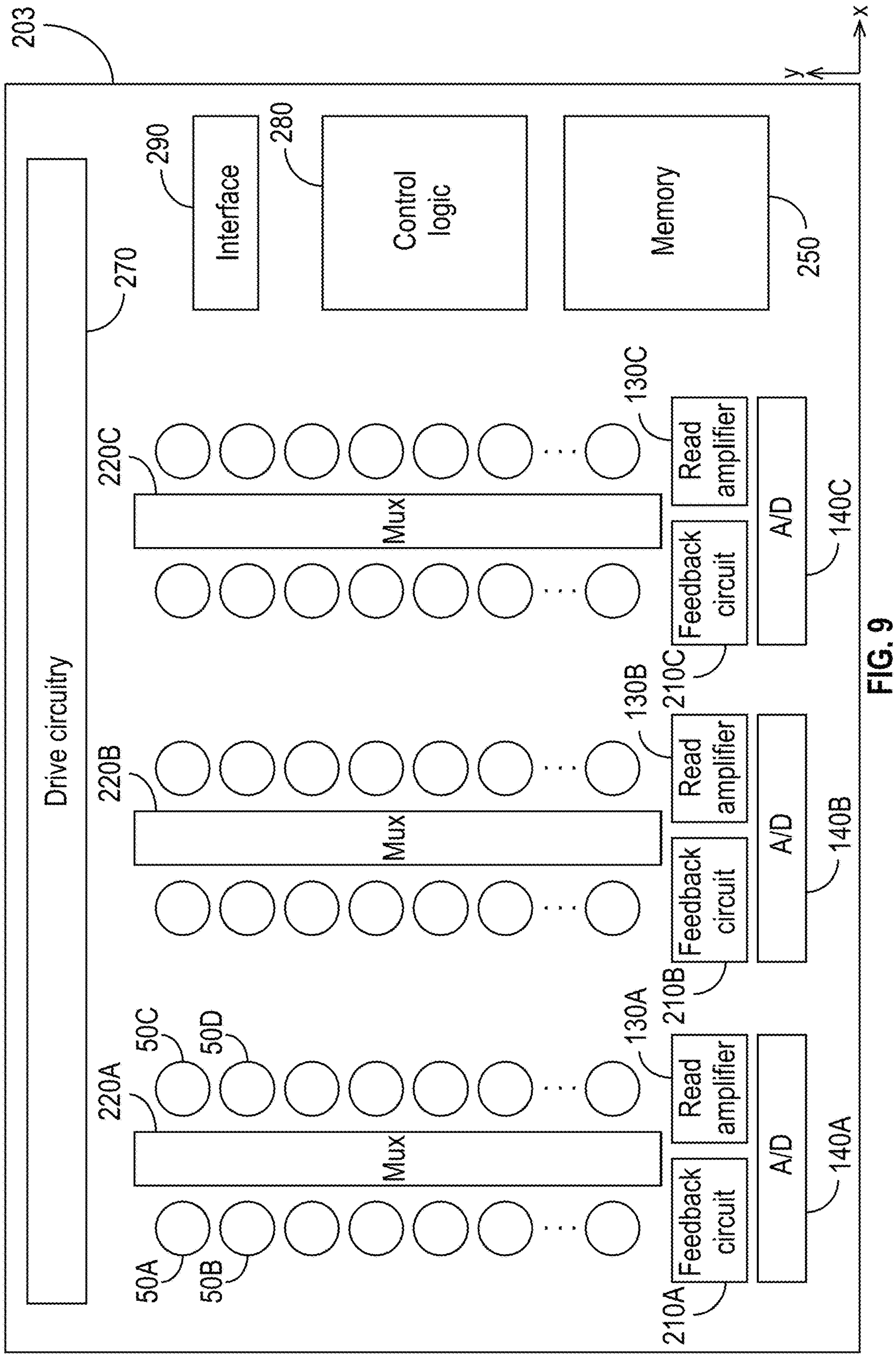
FIG. 9 illustrates an example of a device in accordance with some embodiments.

FIG. 9 illustrates an example of a device 203 in accordance with some embodiments. The device 203 may be an implementation of the system 202 shown in FIG. 8. The device 203 may be, for example, an integrated circuit chip that allows molecules to be detected. FIG. 9 is a diagram showing a plan view (e.g., in an x-y plane perpendicular to the x-z plane shown in FIG. 1 and others herein) of the device 203. As shown, the device 203 includes a plurality of nanopore units 50. To avoid obscuring the drawing, only four nanopore units 50 are labeled: nanopore unit 50A, nanopore unit 50B, nanopore unit 50C, and nanopore unit 50D. As explained in the discussion of FIG. 7, the nanopore units 50 are coupled to multiplexers 220. In FIG. 9, respective pluralities (subsets) of the nanopore units 50 are coupled to the multiplexer 220A, multiplexer 220B, and multiplexer 220C. Coupled to each of the multiplexers 220 (e.g., as illustrated in FIG. 7) is a respective feedback circuit 210, a respective amplifier 130, and a respective analog-to-digital converter 140. Specifically, multiplexer 220A is coupled to feedback circuit 210A, read amplifier 130A, and analog-to-digital converter 140A; multiplexer 220B is coupled to feedback circuit 210B, read amplifier 130B, and analog-to-digital converter 140B; and multiplexer 220C is coupled to feedback circuit 210C, read amplifier 130C, and analog-to-digital converter 140C. The device 203 also includes drive circuitry 270, an interface 290, control logic 280, and memory 250. These components were described above in the discussion of FIGS. 8 and/or 9. That discussion applies here and is not repeated.

Figure 10:
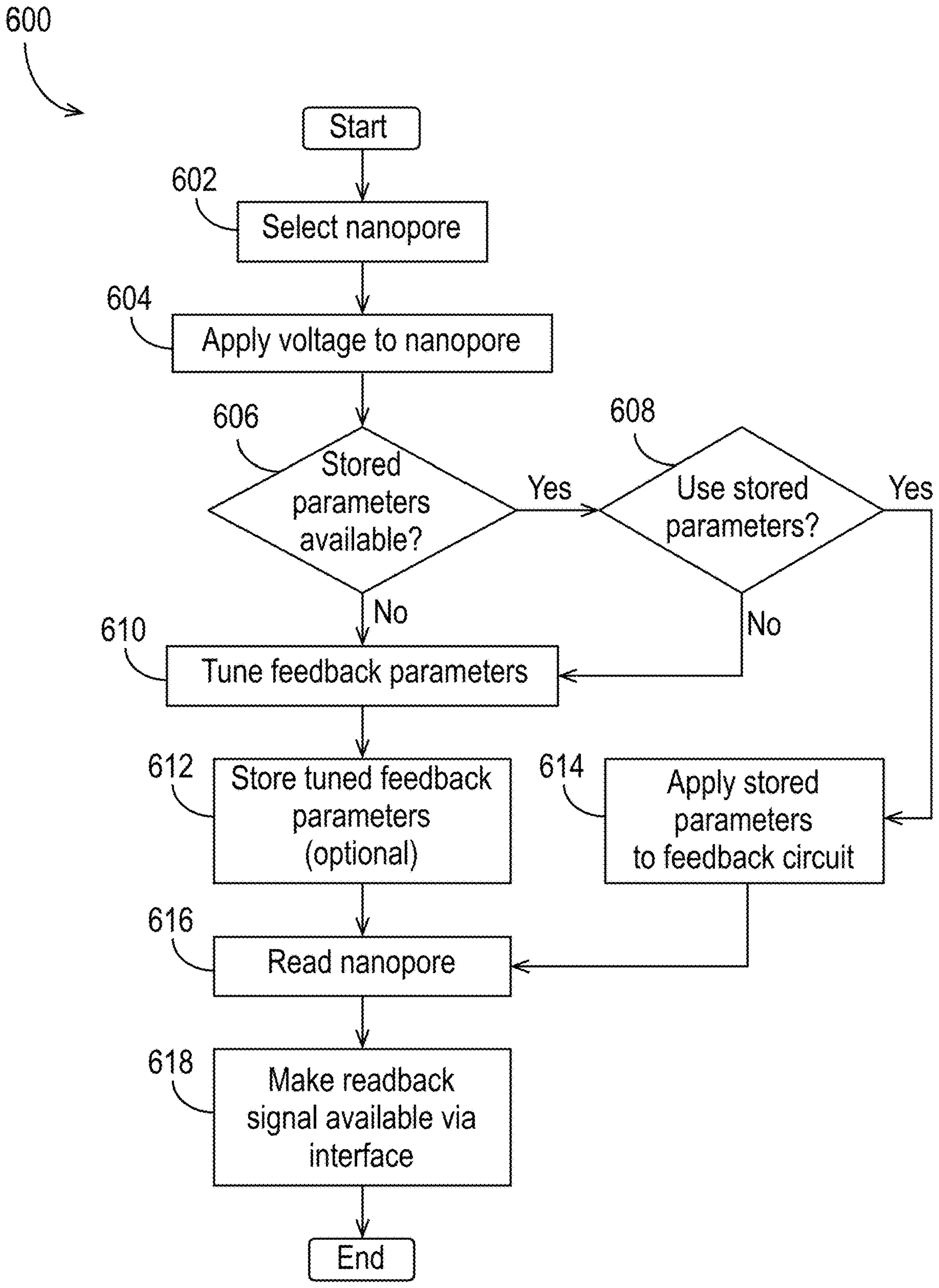
FIG. 10 is a flow diagram illustrating a method of using a molecule detection device or system in accordance with some embodiments.

FIG. 10 is a flow diagram illustrating a method 600 of using a molecule detection device or system in accordance with some embodiments. The method 600 can be performed, for example, by hardware of any of system 201, system 202, or device 203. After the method 600 starts, at block 602, a nanopore 15 is selected for reading/detection. The nanopore 15 may be selected, for example, using the multiplexer 220. At block 604, a voltage is applied to the nanopore 15 (e.g., using the voltage source 150 and the sense electrode 18A and counter electrode 18B). At block 606, it is determined whether stored feedback parameters are available. For example, it may be determined at block 606 whether previously-determined feedback parameters that can be used to configure the feedback circuit 210 to read the selected nanopore 15 are available in memory 250. If so, then at block 608, a decision is made whether to use the stored parameters to configure the feedback circuit 210 to read the selected nanopore 15. If the decision is made to use the stored parameters, then at block 614 the stored parameters are applied to the feedback circuit 210 (e.g., to set some aspect of the operation of the feedback circuit 210, such as, for example, an amplifier gain, capacitance, resistance, voltage, current, frequency response, etc.). The method 600 then proceeds to the block 616, where the selected nanopore 15 is read (e.g., to detect the presence or content of a molecule 20 translocating through the nanopore 15). Reading the nanopore 15 may comprise detecting a characteristic (e.g., current, change in current, voltage, change in voltage, frequency, change in frequency, noise, change in noise, signal-to-noise ratio, etc.) of an output signal of the amplifier 130. As explained above, the result of reading the nanopore 15 can be the delivery of the current Is as the input to the amplifier 130. At block 618, the readback signal obtained from reading the selected nanopore 15 is made available (e.g., via the interface 240 or interface 290). The readback signal may be, for example, the digitized/sampled signal provided by the analog-to-digital converter 140 to the control logic 230 (e.g., as illustrated in FIG. 7). The interface 240 or interface 290 may be connected to a downstream component, such as a data storage device or processing system, for example.

If, at block 606, it is determined that stored parameters are not available, or it is determined at block 608 that the stored parameters are not to be used to read the nanopore 15, at block 610 the feedback parameters are tuned as described further below. The objective of block 610 is to determine the appropriate settings/parameters for the feedback circuit 210 to reduce the effect of the parasitic capacitance 19 at the input to the amplifier 130 on the SNR of the read signal. At block 612, the tuned feedback parameters determined at block 610 may optionally be stored (e.g., in memory 250). The method 600 then proceeds to block 616 and block 618, described above.

The tuning of feedback parameters at block 610 can be performed in any suitable manner. Any characteristic of the amplifier 130 output signal can be detected. This characteristic may be obtained directly from the amplifier 130 or from another component. For example, the feedback circuit 210 may be tuned heuristically to the point of impending instability (e.g., when the output signal Vs or Ds begins to exhibit oscillation indicating instability, which may be detected by the control logic 230), and then backed off slightly so that the output signal remains stable. As another example, the digital data Ds from the analog-to-digital converter 140 may be processed to assess the effect of the settings of the feedback circuit 210 on the SNR (or a proxy for SNR, such as bit error ratio) of the readback signal. As another example, for applications in which the selected nanopore 15 is used to store data, the error rate of the error-correcting code that follows the readback can be used to determine whether the feedback parameters are suitable or should be changed. As yet another example, the interface 240 may provide some version of the readback signal to a downstream user-level software, which may provide an indication of the quality of the data signal. The feedback parameters used by the feedback circuit 210 can then be adjusted based on the information from the user-level software. The tuned value(s) of the feedback parameter(s) may then be stored.

It will be appreciated that there are many ways the analog signal from the amplifier 130 and/or the digital signal from the analog-to-digital converter 140, or processed versions of one or both of them, or information from a downstream system that has assessed signal quality, can be used to determine whether the feedback circuit 210 is providing appropriate feedback at the input to the amplifier 130. The examples provided herein are not intended to be limiting.

Bootstrap

Implementing the approaches described above may warrant additional lithographic steps to fabricate an additional electrode (e.g., a feedback electrode 190). In another approach, referred to as the bootstrap approach, the counter electrode 18B can be directly bootstrapped to the output of the amplifier 130, which can avoid additional lithographic steps during the manufacturing process. The bootstrapping approach can be used for both tunnel and ionic motion-based sensing.

Ordinarily, a bootstrap circuit applies an output of an amplifier to the amplifier input in order to change the input impedance of the amplifier. As described further below, bootstrapping can be used to provide feedback to at least partially cancel the parasitic capacitance 19. In some embodiments, a frequency-selective element (e.g., a bootstrap circuit) is situated between the output of the amplifier 130 and the counter electrode 18B, which allows a fast feedback signal to be fed in to cancel at least a portion of the parasitic capacitance 19 while still allowing enough of a potential difference between the sense electrode 18A and counter electrode 18B to draw ions into the hole 16. Use of, for example, a resistor-capacitor (RC) circuit for bootstrapping allows the nanopore 15 to be biased at low frequencies (bias constant) while also providing a high-frequency voltage component to cancel at least a portion of the parasitic capacitance 19. In other words, the bootstrap circuit acts as a low-pass filter for the bias function and as a high-pass filter to cancel at least some of the parasitic capacitance 19. In some embodiments, the bootstrap signal is provided by the output of the amplifier 130. In some embodiments, the bootstrap signal is provided by the sense electrode 18A.

Figure 11A:
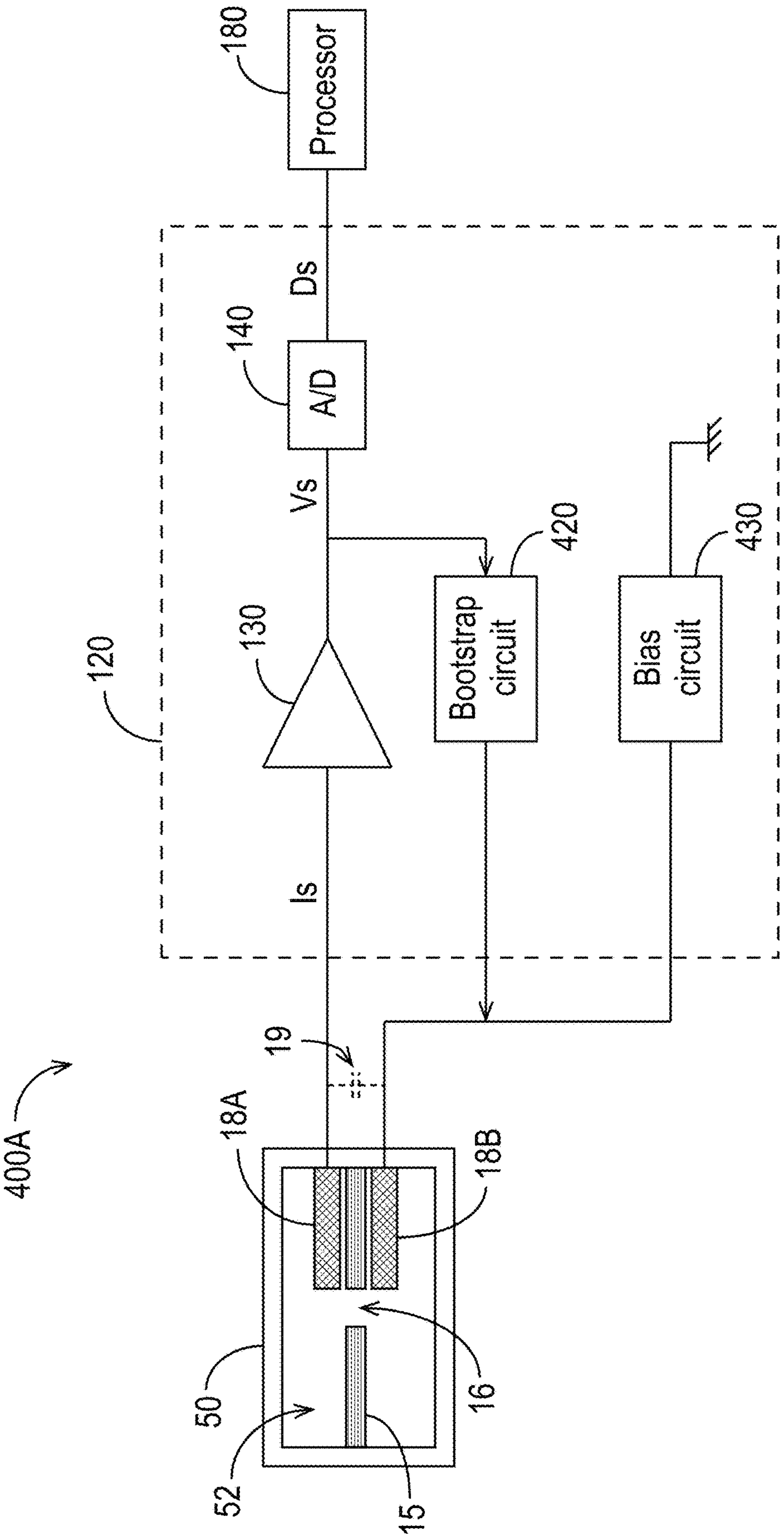
FIG. 11A is a diagram illustrating an example of a system that uses bootstrapping in accordance with some embodiments.

FIG. 11A is a diagram illustrating an example of a system 400A that uses bootstrapping in accordance with some embodiments. As shown in FIG. 11A, the current detected by the sense electrode 18A is measured by the amplifier 130, which may be a low-input-capacitance (high-impedance) buffer amplifier. A bootstrap circuit 420 feeds the output of the amplifier 130 back to the counter electrode 18B such that the injected charge effectively cancels at least a portion the parasitic capacitance 19 between the sense electrode 18A and the counter electrode 18B (illustrated by the parasitic capacitance 19 having a smaller size and being shown in dashed lines in FIG. 11A). A bias circuit 430 is also provided to apply a bias voltage to the counter electrode 18B.

Figure 11B:
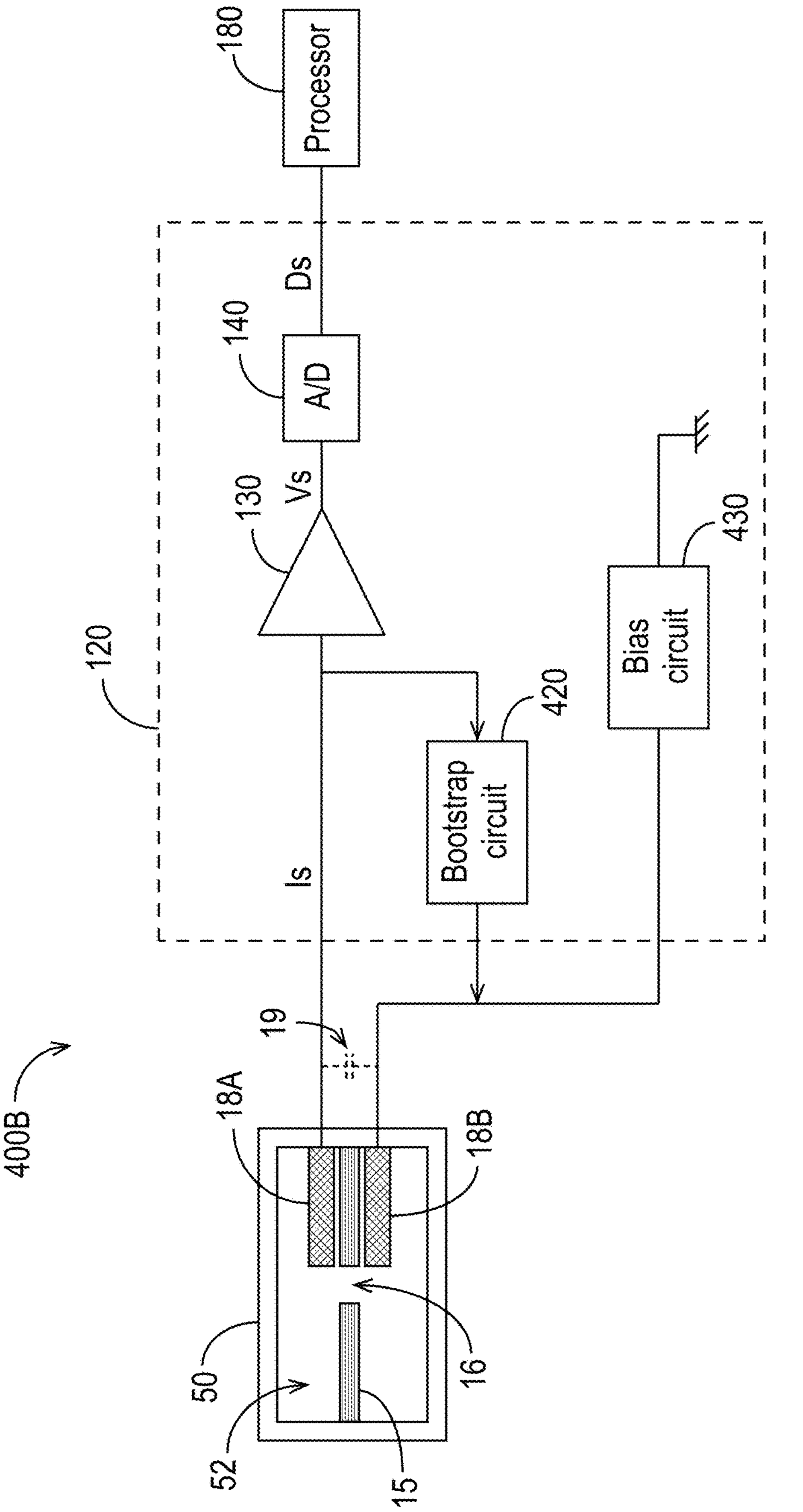
FIG. 11B is a diagram illustrating another example of a system that uses bootstrapping in accordance with some embodiments.

FIG. 11B is a diagram illustrating another example of a system 400B that uses bootstrapping in accordance with some embodiments. As shown in FIG. 11B, a bootstrap circuit 420 feeds the signal on the sense electrode 18A back to the counter electrode 18B such that the injected charge effectively cancels at least a portion the parasitic capacitance 19 between the sense electrode 18A and the counter electrode 18B (illustrated by the parasitic capacitance 19 having a smaller size and being shown in dashed lines in FIG. 11B). As in FIG. 11A, a bias circuit 430 is also provided to apply a bias voltage to the counter electrode 18B.

In FIG. 11A and/or FIG. 11B, the bootstrap circuit 420 may be as simple as a capacitor that has a low impedance at the noise frequencies of interest and feeds the output signal from the amplifier 130 (FIG. 11A) or the signal on the sense electrode 18A (FIG. 11B) to the counter electrode 18B. As a result, the figurative lower plate of the parasitic capacitance 19 (the counter electrode 18B) is (in theory) kept at the same potential as the sense electrode 18A. Because the charge on the parasitic capacitance 19 is proportional to the potential difference $\Delta U$ between the sense electrode 18A and the counter electrode 18B, the smaller the difference, the less charge on the parasitic capacitance 19 and the less input noise to the amplifier 130. The bootstrap circuit 420 thus provides high-pass filtering so that the counter electrode 18B follows the output of the amplifier 130 with the overall bias set by the bias circuit 430.

Figure 12A:
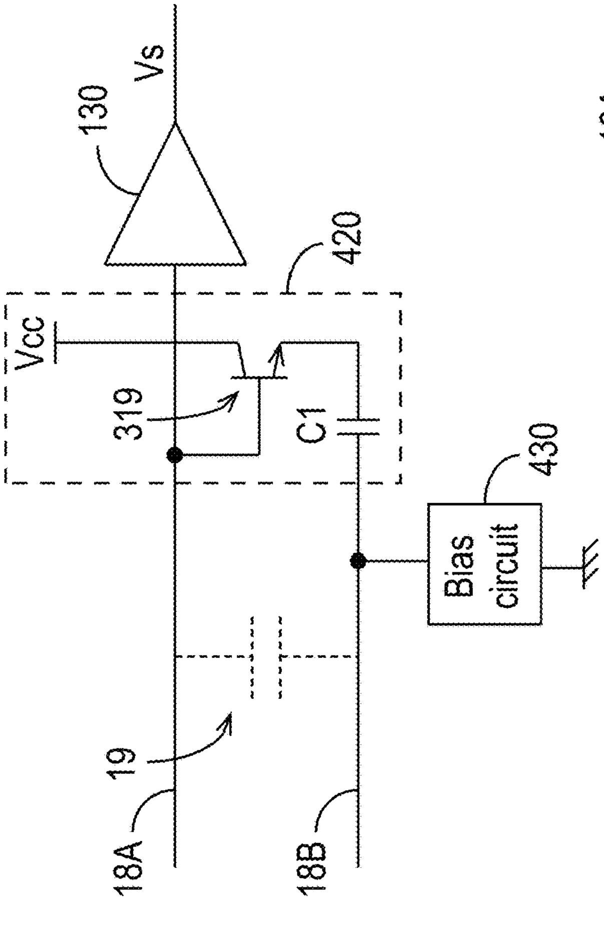
FIG. 12A illustrates an example bootstrap circuit that can provide bootstrapping of the counter electrode in accordance with some embodiments.

FIG. 12A illustrates an example of a bootstrap circuit 420 that can provide bootstrapping of the counter electrode 18B in accordance with some embodiments. As shown, a transistor 319 (e.g., a source follower or emitter follower) can be used along with the capacitor C1 to derive the bootstrap signal from the sense electrode 18A. In the example of FIG. 12A, the transistor 319 is shown as a bipolar junction transistor (BJT), but it is to be appreciated that the transistor 319 can alternatively be a junction-gate field effect transistor (JFET).

Figure 12B:
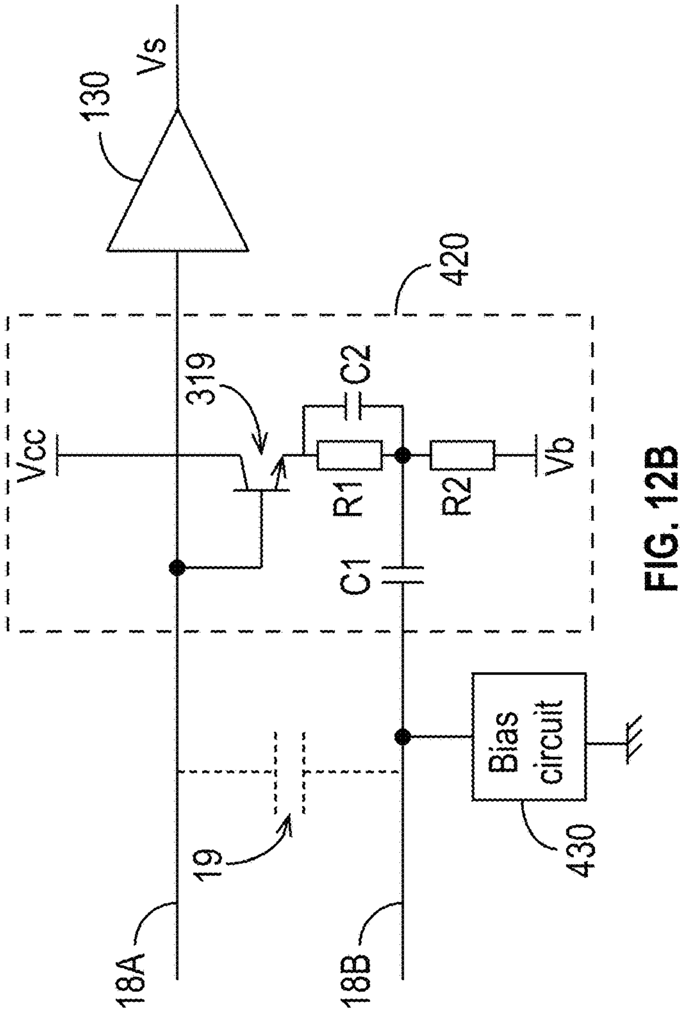
FIG. 12B illustrates the bootstrap circuit of FIG. 12A with full bias circuitry and frequency compensation in accordance with some embodiments.

The amplifier in FIG. 12A is shown without bias circuitry. FIG. 12B illustrates the bootstrap circuit 420 of FIG. 12A with full bias circuitry and frequency compensation for the BJT (transistor 319). In the example of FIG. 12B, the bootstrap circuit 420 incudes, in addition to the capacitor C1, transistor bias circuitry, namely, the resistor R1 in parallel with a capacitor C2, and the resistor R2 connected as shown.

Figure 12C:
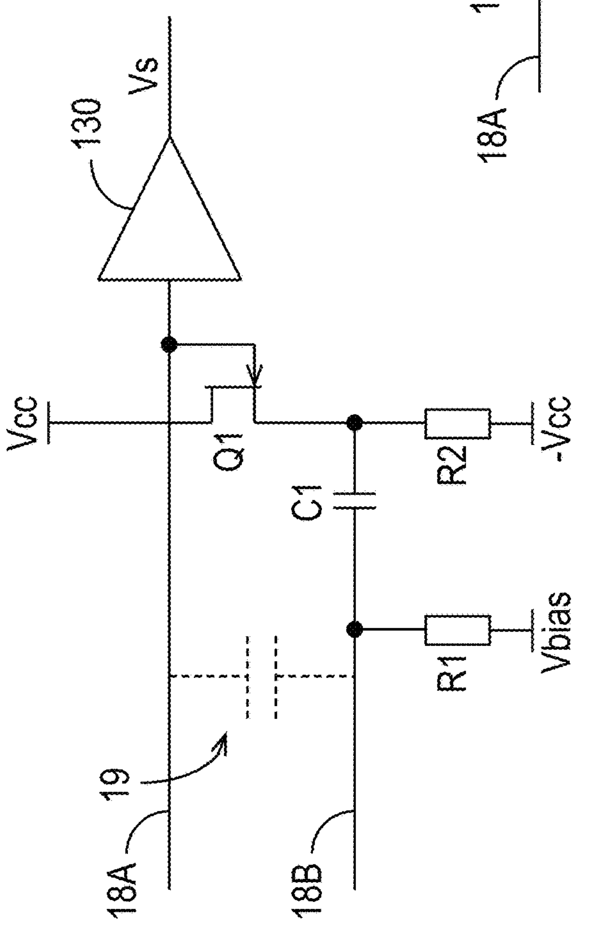
FIG. 12C shows another example bootstrap circuit in accordance with some embodiments.

Other bootstrap circuits can also be used to reduce the parasitic capacitance 19. For example, "The Art of Electronics, 3rd Edition" by Paul Horowitz and Winfield Hill provides circuits that can be used to bootstrap a photodiode and thereby reduce its effective capacitance by a factor of 10 or more. These and other circuits can be adapted and used to bootstrap the counter electrode 18B in nanopore 15 applications. For example, FIG. 12C shows one example circuit based on FIG. 8.82 of "The Art of Electronics, 3rd Edition." FIG. 8.82 and the description thereof in "The Art of Electronics, 3rd Edition" by Paul Horowitz and Winfield Hill is hereby incorporated by reference for all purposes. The example circuit in FIG. 12C includes a follower Q1 coupled to a capacitor C1, resistor R1, and resistor R2 as shown. In the example of FIG. 12C, the bootstrap circuit comprises the follower Q1 and the capacitor C1. The resistor R2 provides bias to the bootstrap circuit. The resistor R1 provides bias to the nanopore 15. The resistor R1 is coupled to a bias voltage source (Vbias).

Figure 12D:
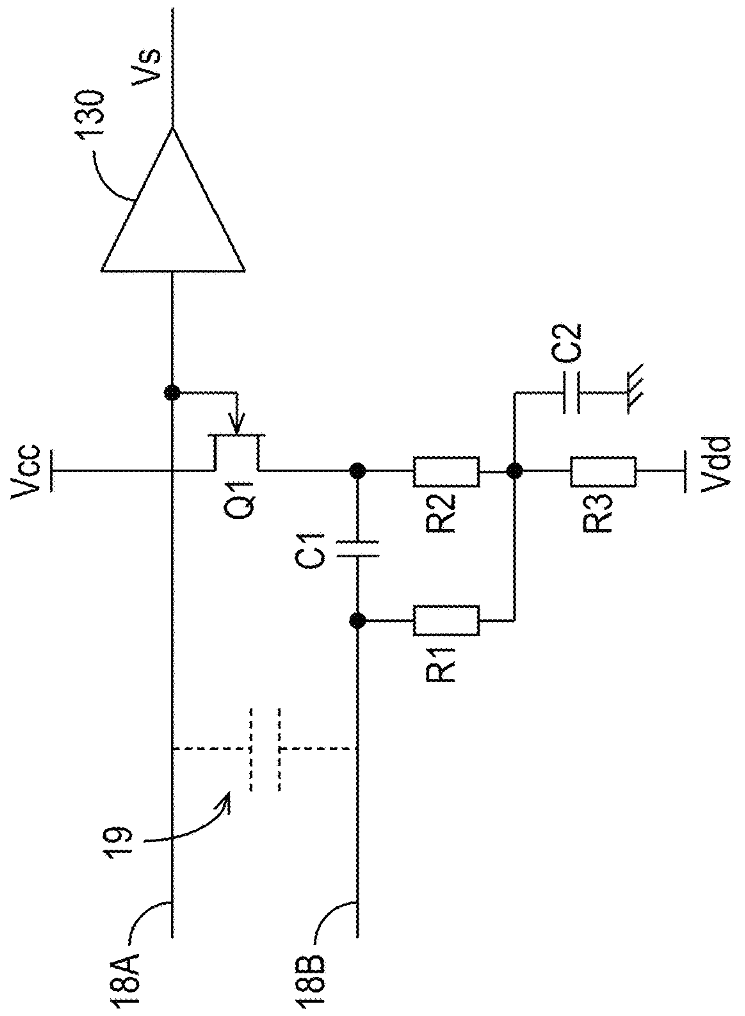
FIG. 12D shows another example bootstrap circuit in accordance with some embodiments.

FIG. 12D shows another example circuit based on FIG. 4*x*.39 of "The Art of Electronics, 3rd Edition." FIG. 4*x*.39 and the description thereof in "The Art of Electronics, 3rd Edition" by Paul Horowitz and Winfield Hill is hereby incorporated by reference for all purposes. The example circuit in FIG. 12D includes a transistor Q1 coupled to an RC circuit that includes resistor R1, resistor R2, resistor R3, capacitor C1, and capacitor C2 connected as illustrated. As will be appreciated by those having ordinary skill in the art, the resistor R2 biases the transistor Q1, and the resistor R1 biases the nanopore 15. The resistor R1 and the capacitor C2 form a low-pass filter. It is to be appreciated that the circuits shown in FIGS. 12A through 12D are examples of suitable bootstrap circuitry. Other bootstrap circuits can be used. The examples shown in FIGS. 12A through 12D are not meant to be limiting. For example, many other types of transistors, amplifiers, or combinations thereof can be used. In addition, or alternatively, other RC circuitry and/or other components can be used.

Figure 13:
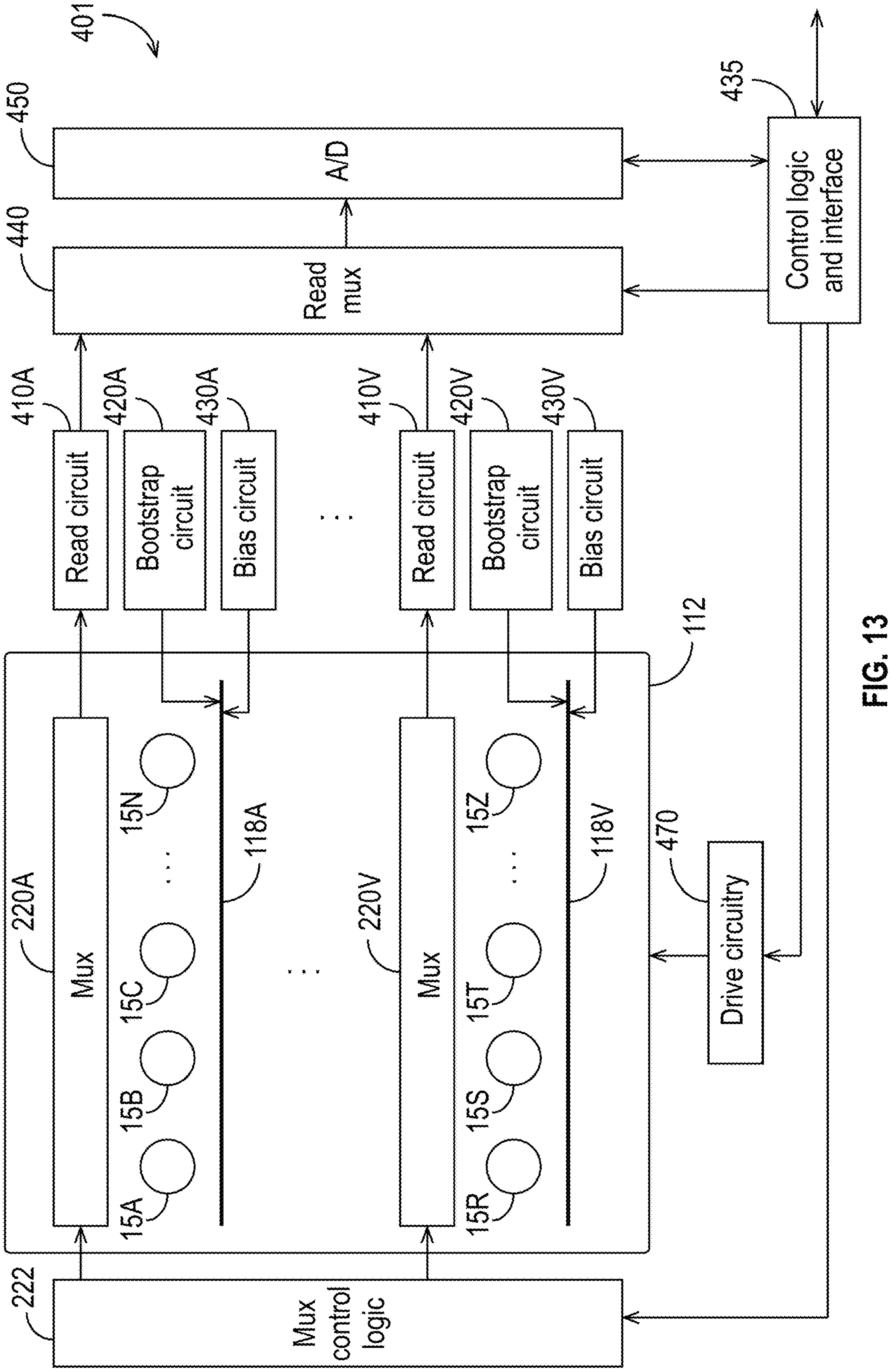
FIG. 13 is an illustration of an example system in accordance with some embodiments.

FIG. 13 is an illustration of an example system 401 in accordance with some embodiments. The system 401 includes an array 112, which includes, among other things, a plurality of nanopores 15. In the example illustrated in FIG. 13, multiple nanopores 15 in the array 112 are coupled to the same counter electrode 18B. In FIG. 13, the nanopore 15A, nanopore 15B, nanopore 15C, . . . , and nanopore 15N share the shared counter electrode 118A, and the nanopore 15R, nanopore 15S, nanopore 15T, . . . , and nanopore 15Z share the shared counter electrode 118V. The shared counter electrode 118A is coupled to the bootstrap circuit 420A and the bias circuit 430A, and the shared counter electrode 118V is coupled to the bootstrap circuit 420V and the bias circuit 430V. The bootstrap circuit 420A, bias circuit 430A, bootstrap circuit 420V, and bias circuit 430V can be configured and can operate as described above in the discussion of FIGS. 11A, 11B, and 12A through 12D.

The array 112 also includes at least one multiplexer 220, which can operate as described above (e.g., to select one nanopore 15 at a time for reading). The nanopore 15 subsets are coupled to respective multiplexers 220. In the example of FIG. 13, the nanopore 15A, nanopore 15B, nanopore 15C, . . . , and nanopore 15N are coupled to the multiplexer 220A, and the nanopore 15R, nanopore 15S, nanopore 15T, . . . , and nanopore 15Z are coupled to the multiplexer 220V. The multiplexer 220A is coupled to and provides a signal to the read circuit 410A, which is coupled to and provides a signal to the read multiplexer 440. Similarly, the multiplexer 220V is coupled to and provides a signal to the read circuit 410V, which is coupled to and provides a signal to the read multiplexer 440. The read circuit 410A and read circuit 410V may comprise a high-impedance buffer amplifier as described above.

The read multiplexer 440 is coupled to and provides a signal to the digitizer 450, which may be, for example, an analog-to-digital converter (e.g., analog-to-digital converter 140 as described above). The read multiplexer 440 and digitizer 450 are coupled to the control logic and interface 435 as shown. The control logic and interface 435 may combine some or all of the functionalities described previously for some or all of the control logic 230, control logic 280, interface 240, and/or interface 290. For example, the control logic and interface 435 may send to and/or receive signals and/or instructions from the drive circuitry 470 and/or the digitizer 450, and/or it may make the results of a measurements/reads of the nanopores 15 available to a downstream system via any suitable interface (e.g., wired or wireless). The control logic and interface 435 is also coupled to the drive circuitry 470, which may be similar or identical to and operate similarly or identically to the drive circuitry 270 described previously. Although FIG. 13 illustrates only a single drive circuitry 470 for the system 401, it is to be appreciated that there may be more than one drive circuitry 470 in the system 401. For example, the multiplexers 220 and drive circuitry 470 may be in a one-to-one relationship, or a single instance of the drive circuitry 470 can be coupled to more than one but fewer than all of the multiplexers 220.

The system 401 also includes multiplexer control logic 222, which may be configured to select one of the multiplexers 220 in the array 112. The multiplexer control logic 222 may be coupled to and controlled by the control logic and interface 435. The control logic and interface 435 may be configured to control the multiplexer control logic 222 to select one of the multiplexers 220, and the selected multiplexer 220 may be configured to cause a selected nanopore 15 to be read.

It is to be appreciated that the system 401 can include fewer or more combinations of components than shown. Moreover, the use of the letters "N," "Z," "V," etc. in the reference numerals is not intended to suggest that the system 401 includes any particular number of any particular component. In general, the system 401 can include any number of each type of component illustrated.

Figure 14:
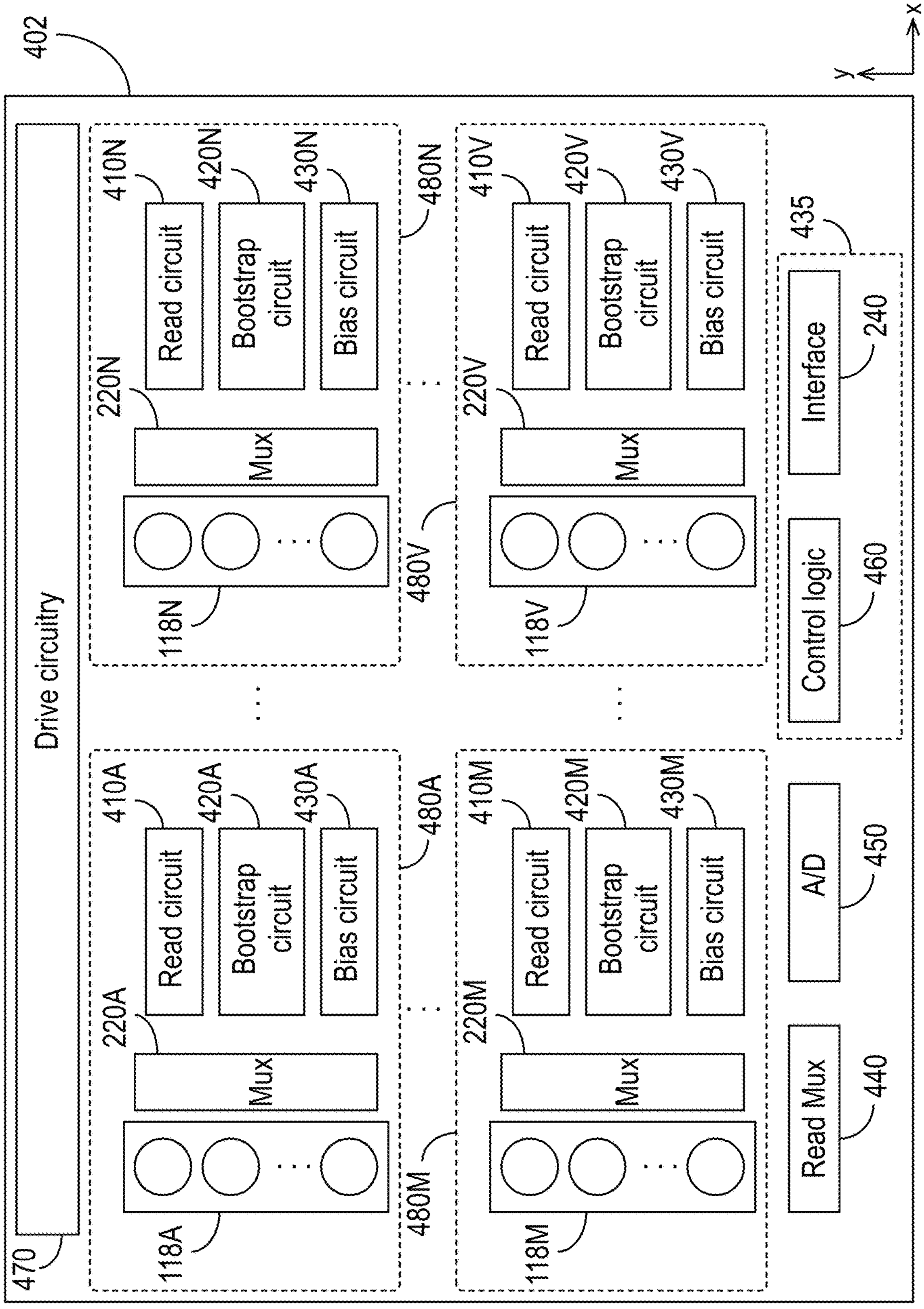
FIG. 14 illustrates an example of a device in accordance with some embodiments.

FIG. 14 illustrates an example of a device 402 in accordance with some embodiments. The device 402 may be an implementation of the system 401 shown in FIG. 13. The device 402 may be, for example, an integrated circuit chip that allows molecules to be detected. FIG. 14 is a diagram showing a plan view (e.g., in an x-y plane perpendicular to the x-z plane shown in FIG. 1 and others herein) of the device 402. Specifically, FIG. 14 is an illustration of components of an integrated circuit chip as seen from below. As shown, the device 402 includes a plurality of component collections, each of which includes a plurality of nanopores 15 (unlabeled to avoid obscuring the drawing, but illustrated as circles as in other drawings), a shared counter electrode 118, a multiplexer 220, a read circuit 410, a bootstrap circuit 420, and a bias circuit 430. FIG. 14 illustrates the component collection 480A, which includes a first plurality of nanopores 15, the shared counter electrode 118A, the multiplexer 220A, the read circuit 410A, the bootstrap circuit 420A, and the bias circuit 430A; the component collection 480N, which includes a second plurality of nanopores 15, the shared counter electrode 118N, the multiplexer 220N, the read circuit 410N, the bootstrap circuit 420N, and the bias circuit 430N; the component collection 480M, which includes a third plurality of nanopores 15, the shared counter electrode 118M, the multiplexer 220M, the read circuit 410M, the bootstrap circuit 420M, and the bias circuit 430M; and the component collection 480V, which includes a fourth plurality of nanopores 15, the shared counter electrode 118V, the multiplexer 220V, the read circuit 410V, the bootstrap circuit 420V, and the bias circuit 430V.

FIG. 14 also illustrates the drive circuitry 470, which, as explained above, may be shared by the nanopores 15. The control logic and interface 435 block includes both control logic 460 and the interface 240. The interface 240 may be configured and may operate as described above. The control logic 460 may include the multiplexer control logic 222 shown in FIG. 13. The read multiplexer 440 is coupled to and provides a signal to the digitizer 450, shown as an analog-to-digital converter. The read multiplexer 440 and digitizer 450 are coupled to the control logic and interface 435 as described above in the discussion of FIG. 13.

It is to be appreciated that the device 402 can include fewer or more combinations of components than shown. Moreover, the use of the letters "M," "N," and "V" in the reference numerals is not intended to suggest that the device 402 includes any particular number of any particular component. In general, the device 402 can include any number of each type of component illustrated. Moreover, the illustration of separate blocks in FIG. 14 is for convenience. It is to be appreciated that certain of the blocks can be combined (e.g., the bootstrap circuit and bias circuit for a particular collection of components can be combined into one circuit).

It is to be appreciated that two or more of the approaches described above can be used together. For example, a system can include: (a) a feedback circuit coupled to the sense electrode 18A, and/or (c) a bootstrap circuit coupled to the counter electrode 18B.

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms "a," "an" and "the" do not exclude plural referents unless otherwise specified. The word "or" is to be interpreted as inclusive unless otherwise specified. Thus, the phrase "A or B" is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

To the extent that the terms "include(s)," "having," "has," "with," and variants thereof are used in the detailed description or the claims, such terms are intended to be inclusive in a manner similar to the term "comprising," i.e., meaning "including but not limited to."

The terms "exemplary" and "embodiment" are used to express examples, not preferences or requirements.

The term "coupled" is used herein to express a direct connection/attachment as well as a connection/attachment through one or more intervening elements or structures.

The terms "over," "under," "between," and "on" are used herein refer to a relative position of one feature with respect to other features. For example, one feature disposed "over" or "under" another feature may be directly in contact with the other feature or may have intervening material. Moreover, one feature disposed "between" two features may be directly in contact with the two features or may have one or more intervening features or materials. In contrast, a first feature "on" a second feature is in contact with that second feature.

The term "substantially" is used to describe a structure, configuration, dimension, etc. that is largely or nearly as stated, but, due to manufacturing tolerances and the like, may in practice result in a situation in which the structure, configuration, dimension, etc. is not always or necessarily precisely as stated. For example, describing two lengths as "substantially equal" means that the two lengths are the same for all practical purposes, but they may not (and need not) be precisely equal at sufficiently small scales (e.g., if the units of a measurement are meters, two features having lengths of 1.000 m and 1.001 m would have substantially equal lengths). As another example, a structure that is "substantially vertical" would be considered to be vertical for all practical purposes, even if it is not precisely at 90 degrees relative to horizontal.

The drawings are not necessarily to scale, and the dimensions, shapes, and sizes of the features may differ substantially from how they are depicted in the drawings.

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

The invention claimed is:

1. A system for detecting molecules, the system comprising:
- an array comprising a plurality of nanopore units, each of the plurality of nanopore units comprising a nanopore, a sense electrode, and a counter electrode;
- drive circuitry coupled to the array of nanopore units;
- an amplifier;
- a multiplexer coupled to the array of nanopore units and to an input of the amplifier;
- a feedback circuit coupled to an output of the amplifier and to the input of the amplifier; and
- control logic coupled to the feedback circuit and to the multiplexer and configured to:
  - control the multiplexer to select a first nanopore unit of the plurality of nanopore units for reading, and
  - configure the feedback circuit to provide a first amount of feedback for the first nanopore unit.

2. The system recited in claim 1, wherein the first amount of feedback is:
- (a) dependent on an identity of the first nanopore unit, and/or
- (b) applicable to the first nanopore unit and at least one other nanopore unit in the array.

3. The system recited in claim 1, further comprising memory coupled to the control logic, and wherein the control logic is further configured to:
- retrieve information from the memory, the information associated with a prior configuration of the feedback circuit.

4. The system recited in claim 3, wherein the prior configuration of the feedback circuit was a custom configuration for the first nanopore unit.

5. The system recited in claim 1, further comprising tuning logic coupled to the feedback circuit, wherein the tuning logic is configured to:
- adjust at least one parameter of the feedback circuit to increase or decrease the first amount of feedback.

6. The system recited in claim 1, further comprising tuning logic coupled to the feedback circuit, wherein the tuning logic is configured to:
- increase the first amount of feedback,
- detect an onset of instability in an amplifier output signal, and
- decrease the first amount of feedback in response to the detected onset of instability, thereby settling the first amount of feedback at a tuned amount of feedback.

7. The system recited in claim 6, further comprising memory coupled to the tuning logic, and wherein the tuning logic is further configured to:
- store configuration information in the memory, the configuration information associated with the tuned amount of feedback.

8. The system recited in claim 7, wherein the control logic is coupled to the memory, and wherein the control logic is further configured to retrieve the configuration information from the memory and to configure the feedback circuit to provide the tuned amount of feedback for the first nanopore unit.

9. The system recited in claim 1, wherein the control logic is further configured to:
- control the multiplexer to select a second nanopore unit of the plurality of nanopore units, and
- configure the feedback circuit to provide a second amount of feedback for the second nanopore unit.

10. The system recited in claim 9, wherein the second amount of feedback differs from the first amount of feedback.

11. The system recited in claim 9, further comprising memory coupled to the control logic, and wherein the control logic is further configured to:
- retrieve first information from the memory, the first information associated with a prior configuration of the feedback circuit for the first nanopore unit, and
- retrieve second information from the memory, the second information associated with a prior configuration of the feedback circuit for the second nanopore unit.

12. The system recited in claim 9, further comprising tuning logic coupled to the feedback circuit, wherein the tuning logic is configured to:
- adjust at least one parameter of the feedback circuit to increase or decrease the first amount of feedback, and/or
- adjust the at least one parameter of the feedback circuit to increase or decrease the second amount of feedback.

13. The system recited in claim 9, further comprising tuning logic coupled to the feedback circuit, wherein the tuning logic is configured to adjust at least one parameter of the feedback circuit to:
- (a) provide a same amount of feedback for the first nanopore unit and the second nanopore unit, and/or
- (b) provide a customized amount of feedback depending on an identity of a nanopore unit selected by the multiplexer.

14. The system recited in claim 9, wherein the first amount of feedback is substantially equal to the second amount of feedback.

15. A method of reducing noise in a nanopore signal at an input of an amplifier, the method comprising:
- selecting, via a multiplexer controlled by control logic, a first nanopore of a plurality of nanopores, wherein the first nanopore is coupled to the amplifier;

applying a voltage to the first nanopore to produce the nanopore signal at the input of the amplifier;

configuring, by the control logic, an aspect of a feedback circuit coupled to and situated between an output of the amplifier and the input of the amplifier;

detecting a characteristic of an amplifier output signal;

adjusting, by the control logic, the aspect of the feedback circuit in response to the detected characteristic of the amplifier output signal; and the feedback circuit injecting a feedback signal at the input of the amplifier.

16. The method of claim 15, wherein the aspect of the feedback circuit is a capacitance.

17. The method of claim 15, wherein the characteristic of the amplifier output signal comprises at least one of:

(a) a signal-to-noise ratio;

(b) an error rate associated with an error correcting code protecting data represented by the nanopore signal;

(c) a downstream process or component determining the characteristic of the amplifier output signal;

(d) a stability;

(e) an amount of oscillation.

18. The method of claim 15, wherein detecting the characteristic of the amplifier output signal comprises processing a digitized version of the amplifier output signal.

19. The method of claim 15, wherein the characteristic of the amplifier output signal comprises a stability, and wherein adjusting the aspect of the feedback circuit in response to the detected characteristic of the amplifier output signal comprises:

adjusting the aspect of the feedback circuit to increase an amount of feedback provided at the input of the amplifier;

detecting an onset of instability in the amplifier output signal after adjusting the aspect of the feedback circuit to increase the amount of feedback provided at the input of the amplifier; and in response to detecting the onset of instability in the amplifier output signal, adjusting the aspect of the feedback circuit to decrease the amount of feedback provided at the input of the amplifier.

20. The method of claim 19, wherein detecting the onset of instability in the amplifier output signal comprises detecting oscillations in the amplifier output signal.

21. The method of claim 15, further comprising:

determining an optimized aspect of the feedback circuit by iteratively (a) detecting the characteristic of the amplifier output signal, and (b) adjusting the aspect of the feedback circuit in response to the detected characteristic of the amplifier output signal.

22. The method of claim 21, further comprising:

storing information identifying the optimized aspect of the feedback circuit in memory.

23. The method of claim 22, further comprising:

retrieving the information identifying the optimized aspect of the feedback circuit from the memory, and wherein configuring the aspect of the feedback circuit comprises configuring the aspect in accordance with the information identifying the optimized aspect of the feedback circuit.

* * * * *